United States Patent [19]
Levine et al.

[11] Patent Number: 6,020,135
[45] Date of Patent: Feb. 1, 2000

[54] P53-REGULATED GENES

[75] Inventors: Arnold J. Levine, Princeton, N.J.; Maureen Elizabeth Murphy, Blue Bell, Pa.; David H. Mack, Menlo Park, Calif.; Kurt Carlyle Gish, Sunnyvale, Calif.; Edward Yat Wah Tom, Sacramento, Calif.

[73] Assignees: Affymetrix, Inc.; Princeton University

[21] Appl. No.: 09/049,025

[22] Filed: Mar. 27, 1998

[51] Int. Cl.⁷ .............................. C17Q 1/68; C07H 21/04
[52] U.S. Cl. .............................. 435/6; 435/375; 536/23.1; 536/24.31
[58] Field of Search .............................. 435/6, 69.1, 183, 435/463, 325, 375; 536/23.1, 23.2, 24.31; 514/44

[56] References Cited

U.S. PATENT DOCUMENTS 5,700,637  12/1997  Southern ..................................... 435/6

FOREIGN PATENT DOCUMENTS

| | | |
|---|---|---|
| 0 390 323 | 10/1990 | European Pat. Off. |
| 89/10977 | 11/1989 | WIPO. |
| 94/18992 | 9/1994 | WIPO. |
| 95/19369 | 7/1995 | WIPO. |
| 99/01581 | 1/1999 | WIPO. |

OTHER PUBLICATIONS

O'Connor et al., Cancer Research 57, 4285–4300 (Oct. 1, 1997).
Li et al., Proc. of the American Assoc. for Cancer Res. Annual Meeting 37 (0):p. 299 (Mar. 1996).
Weller et al. Int. J. Cancer (Pred. Oncol.): 79, 640–644 (1998).
Weiss, G. DDT vol. 1, No. 12, pp. 529–532 (Dec. 1996).
Lloyd, A.J. DDT vol. 2, No. 10, pp. 397–398 (Oct. 1997).
Goldman, M.E. DDT vol. 2, No. 9, pp. 357–358 (Sep. 1997).
Schena et al. "Parallel Human Genome Analysis: Microarray–Based Expression Monitoring of 1000 Genes" Proceedings of the National Academy of Sciences of USA, vol. 93, No. 20, Oct. 1, 1996, pp. 10614–10619.
Madden et al. "SAGE transcription profiles for P53–dependent growth regulation" Oncogene, vol. 15, No. 9, Aug. 1, 1997, pp. 1079–1085.
Madden et al. "Induction of Cell Growth Regulatory Genes by P53" Cancer Research, vol. 56, No. 23, Dec. 1, 1996, pp. 5384–5390.
Beaudry et al. "Therapeutic targeting of the P53 tumor suppressor gene" Current Opinion in Biotechnology, vol. 7, No. 7, Dec. 1, 1996, pp. 592–600.
Polyak et al. "A model for p53–induced apoptosis" Nature, vol. 389, Sep. 18, 1997, pp. 300–305.
Lin Zhang et al. "Gene Expression Profiles in Normal and Cancer Cells" Science, vol. 276, May 23, 1997, 1268–1272.

*Primary Examiner*—John L. LeGuyader
*Assistant Examiner*—Mark L. Shibuya
*Attorney, Agent, or Firm*—Banner & Witcoff, Ltd.

[57] ABSTRACT

Many genes are identified as being p53-regulated which were not heretofore known to be p53-regulated. This includes both genes whose expression is induced and genes whose expression is repressed by the expression of wild-type p53. Monitoring expression of these genes is used to provide indications of p53 status in a cell. Such monitoring can also be used to screen for useful anti-cancer therapeutics, as well as for substances which are carcinogenic. Defects in p53 can be bypassed by supplying p53 induced genes to cells. Defects in p53 can also be bypassed by supplying antisense constructs to p53-repressed genes.

24 Claims, 20 Drawing Sheets

FIG. 1A

| Gene # | Intensity in EB 1 | Intensity in EB | PM > MM in EB | PM > MM in EB 1 | Induced Ratio | EST # | Accession # | EST? | SAGE? |
|---|---|---|---|---|---|---|---|---|---|
| 1 | 1450 | -36.7 | 0.85 | 0.35 | | Hsa.140 | M87789 gene 1 | ✓ | |
| 2 | 1450 | 107 | 1 | 0.7 | 14 | Hsa.1534 | J00231 gene 1 | | |
| 3 | 1220 | -30.9 | 0.95 | 0.45 | | Hsa.20518 | R85690 3' UTR 2a | ✓ | |
| 4 | 1070 | 86.4 | 1 | 0.7 | 12 | Hsa.8219 | R46753 3' UTR 2a | ✓ | |
| 5 | 1010 | 155 | 0.95 | 0.7 | 6 | Hsa.2820 | Z31695 gene 1 | | |
| 6 | 1010 | 53.4 | 1 | 0.67 | 19 | Hsa.41163 | U06088 gene 1 | | |
| 7 | 864 | 46.4 | 1 | 0.81 | 19 | Hsa.2836 | R71870 3' UTR 1 | ✓ | |
| 8 | 862 | 148 | 0.9 | 0.9 | 6 | Hsa.2551 | X57348 gene 1 | | ✓ |
| 9 | 788 | 137 | 0.85 | 0.7 | 6 | Hsa.41123 | J00277 gene 1 | | |
| 10 | 714 | 139 | 1 | 0.95 | 5 | Hsa.13765 | X55740 gene 1 | | ✓ |
| 11 | 695 | -4.82 | 1 | 0.62 | | Hsa.224 | U03106 gene 1 | | ✓ |
| 12 | 645 | 98.6 | 0.9 | 0.8 | 7 | Hsa.8966 | X80200 gene 1 | | |
| 13 | 599 | -3.31 | 1 | 0.42 | | Hsa.224 | U03106 gene 1 | | |
| 14 | 582 | 45.8 | 0.85 | 0.55 | 13 | Hsa.1556 | L13738 gene 1 | | |
| 15 | 572 | 10.5 | 0.85 | 0.6 | 54 | Hsa.9103 | T67406 3' UTR 2a | ✓ | |
| 16 | 569 | 46.4 | 0.95 | 0.52 | 12 | Hsa.3081 | H20434 3' UTR 1 | | |
| 17 | 538 | -99.1 | 0.93 | 0.47 | | Hsa.936 | Z20656 gene 1 | | |
| 18 | 515 | 25.5 | 0.95 | 0.5 | 20 | Hsa.866 | M21389 gene 1 | ✓ | |
| 19 | 480 | 48.1 | 0.95 | 0.85 | 10 | Hsa.36025 | H28050 3' UTR 2a | ✓ | |
| 20 | 473 | 31.7 | 0.9 | 0.7 | 15 | Hsa.1464 | M35878 gene 1 | | |
| 21 | 463 | 6.03 | 0.9 | 0.4 | | Hsa.1971 | T51913 3' UTR 1 | ✓ | |
| 22 | 445 | -9.41 | 0.94 | 0.47 | | Hsa.3011 | X63380 gene 1 | | |

| | | | | | | |
|---|---|---|---|---|---|---|
| 23 | 437 | -6.03 | 0.9 | 0.5 | Hsa.21756 | R94967 3' UTR 2a | ☐ |
| 24 | 385 | 32.8 | 0.95 | 0.55 | 12 Hsa.1069 | T41265 3' UTR 1 | ☑ |
| 25 | 383 | 61.2 | 0.8 | 0.65 | 6 Hsa.32222 | R69448 3' UTR 2a | ☑ |
| 26 | 383 | 21.9 | 1 | 0.75 | 17 Hsa.2611 | R59199 3' UTR 1 | ☑ |
| 27 | 376 | 10.5 | 0.94 | 0.59 | 36 Hsa.620 | M27138 gene 1 | ☐ |
| 28 | 364 | 61.1 | 0.9 | 0.6 | 6 Hsa.401 | X82166 gene 1 | ☐ |
| 29 | 353 | -34.4 | 0.85 | 0.5 | Hsa.936 | Z20656 gene 1 | ☐ |
| 30 | 341 | -42.5 | 0.95 | 0.48 | Hsa.3064 | X05615 gene 1 | ☐ |
| 31 | 331 | 21.1 | 0.81 | 0.52 | 16 Hsa.243 | U01147 gene 1 | ☑ |
| 32 | 329 | 54 | 1 | 0.94 | 6 Hsa.1432 | M64347 gene 1 | ☐ |
| 33 | 313 | 55.6 | 0.95 | 0.8 | 6 Hsa.32445 | R71505 3' UTR 2a | ☑ |
| 34 | 293 | 13.3 | 0.9 | 0.55 | 22 Hsa.3348 | X15880 gene 1 | ☐ |
| 35 | 291 | 18.7 | 0.9 | 0.7 | 16 Hsa.2000 | L16242 gene 1 | ☑ |
| 36 | 288 | -18.3 | 0.9 | 0.45 | Hsa.8468 | H19201 3' UTR 2a | ☐ |
| 37 | 287 | 17 | 0.9 | 0.62 | 17 Hsa.169 | U02388 gene 1 | ☐ |
| 38 | 276 | 40.7 | 1 | 0.78 | 7 Hsa.41094 | L18920 gene 1 | ☐ |
| 39 | 275 | 37.4 | 0.9 | 0.9 | 7 Hsa.2054 | X70340 gene 1 | ☐ |
| 40 | 269 | 38.1 | 0.95 | 0.8 | 7 Hsa.21901 | R49565 3' UTR 1 | ☐ |
| 41 | 252 | -30.5 | 0.76 | 0.48 | Hsa.1876 | X54156 gene 1 | ☐ |
| 42 | 250 | 48.2 | 0.9 | 0.55 | 5 Hsa.2827 | Z11502 gene 1 | ☐ |
| 43 | 247 | 25.5 | 1 | 0.69 | 10 Hsa.2835 | X07696 gene 1 | ☑ |

FIG. 1C

| Gene Description | Induced |
|---|---|
| IG GAMMA-1 CHAIN C REGION (HUMAN). | |
| Human Ig gamma3 heavy chain disease OMM protein mRNA. | |
| 274912 MYELIN TRANSCRIPTION FACTOR 1 (Homo sapiens) | |
| 152524 CYCLIN-DEPENDENT KINASE INHIBITOR 1 (Homo sapiens) | |
| H.sapiens mRNA for 43 kDa inositol polyphosphate 5-phosphatase. | |
| Human N-acetylgalactosamine 6-sulphatase (GALNS) gene, exon 14. | |
| 155730 KERATIN, TYPE I CYTOSKELETAL 17 (HUMAN). | |
| H.sapiens mRNA (clone 9112), kinase related protein. | |
| c-Ha-ras1 proto-oncogene, complete coding sequence, Human (genomic clones lambda-[SK2-T2, HS578T]; cDNA clones RS-[3, 4, 6]). | |
| Human placental cDNA coding for 5'nucleotidase (EC 3.1.3.5). | |
| Human wild-type p53 activated fragment-1 (WAF1) mRNA, complete cds. | |
| H.sapiens MLN62 mRNA. | |
| Human wild-type p53 activated fragment-1 (WAF1) mRNA, complete cds. | |
| Human activated p21cdc42Hs kinase (ack) mRNA, complete cds. | |
| 81780 COMPLEMENT C4 PRECURSOR (Homo sapiens) | |
| 172486 clone, mRNA for tuberin, or TSC2 gene. | |
| Homo sapiens of cardiac alpha-myosin heavy chain gene. | |
| KERATIN, TYPE II CYTOSKELETAL 5 (HUMAN);contains MSR1 repetitive element;. | |
| 182000 FK506-BINDING PROTEIN PRECURSOR (Mus musculus) | |
| Human insulin-like growth factor-binding protein-3 gene, complete cds, clone HL1006d. | |
| 72466 ALPHA CRYSTALLIN B CHAIN (HUMAN). | |
| Homo sapiens mRNA for serum response factor-related protein, RSRFR2. | |

| |
|---|
| 198656 HEPATOCYTE GROWTH FACTOR-LIKE PROTEIN PRECURSOR (Homo sapiens) |
| 62461 SMALL NUCLEAR RIBONUCLEORPROTEIN Particle N (SNRPN), contains MSR1 repetitive element,. |
| 155335 INTEGRIN ALPHA-3 (Homo sapiens) |
| 41792 TUBULIN BETA-2 CHAIN (HUMAN);. |
| Human estradiol 17 beta-dehydrogenase gene, complete cds. |
| H.sapiens mRNA for cystathionine-beta-synthase. |
| Homo sapiens of cardiac alpha-myosin heavy chain gene. |
| Human mRNA for thyroglobulin. |
| Human guanine nucleotide regulatory protein (ABR) mRNA, complete cds. |
| Human novel growth factor receptor mRNA, 3' cds. |
| 142899 DNA-DIRECTED RNA POLYMERASE III LARGEST SUBUNIT (Plasmodium falciparum) |
| Human mRNA for collagen VI alpha-1 C-terminal globular domain. |
| Homo sapiens sodium channel type I, beta subunit (SCN1B) mRNA, complete cds. |
| 50887 GUANINE NUCLEOTIDE DISSOCIATION STIMULATOR RALGDSA (Mus musculus) |
| Human cytochrome P450 4F2 (CYP4F2) mRNA, complete cds. |
| Human MAGE-2 gene exons 1-4, complete cds. |
| H.sapiens mRNA for transforming growth factor alpha. |
| 38251 H.sapiens HSJ1 mRNA. |
| p53 |
| H.sapiens mRNA for intestine-specific annexin. |
| KERATIN, TYPE I CYTOSKELETAL 15 (HUMAN);contains MER20 repetitive element ;. |

FIG. 1E

| Gene # | Intensity in EB 1 | Intensity in EB | PM > MM in EB | PM > MM in EB 1 | PM > MM in EB | Induced Ratio | EST # | Accession # | EST? | SAGE? |
|---|---|---|---|---|---|---|---|---|---|---|
| 44 | 245 | 26.2 | | 0.8 | 0.55 | 9 | Hsa.35663 | H24346 3' UTR 2a | ☑ | |
| 45 | 245 | 19.6 | | 0.9 | 0.5 | 12 | Hsa.3189 | U17280 gene 1 | | |
| 46 | 239 | 47.6 | | 0.9 | 1 | 5 | Hsa.1915 | L06419 gene 1 | ☑ | |
| 47 | 232 | 32.8 | | 0.85 | 0.5 | 7 | Hsa.33725 | H04238 3' UTR 2a | ☑ | |
| 48 | 225 | -53.5 | | 0.85 | 0.4 | | Hsa.693 | L31409 gene 1 | | |
| 49 | 222 | 18.7 | | 0.94 | 0.71 | 12 | Hsa.2835 | X07696 gene 1 | ☑ | |
| 50 | 218 | -0.125 | | 1 | 0.38 | | Hsa.2072 | Y00406 gene 1 | | |
| 51 | 217 | -28.8 | | 0.9 | 0.43 | | Hsa.1159 | R85613 3' UTR 1 | ☑ | |
| 52 | 215 | -13.5 | | 0.82 | 0.71 | | Hsa.19576 | T98002 3' UTR 2a | ☑ | |
| 53 | 212 | -22.4 | | 0.81 | 0.38 | | Hsa.407 | M95167 gene 1 | ☑ | |
| 54 | 210 | 39.5 | | 1 | 0.8 | 5 | Hsa.31500 | R62945 3' UTR 2a | ☑ | |
| 55 | 204 | -2.31 | | 0.86 | 0.43 | | Hsa.2625 | Z18951 gene 1 | | |
| 56 | 199 | 8.4 | | 0.85 | 0.4 | | Hsa.3344 | M74509 gene 1 | ☑ | |
| 57 | 199 | 32 | | 0.85 | 0.5 | 6 | Hsa.3893 | R42765 3' UTR 2a | | |
| 58 | 198 | 15.2 | | 0.86 | 0.62 | 13 | Hsa.2112 | L07597 gene 1 | ☑ | |
| 59 | 194 | 11.6 | | 0.92 | 0.33 | 17 | Hsa.1382 | U06643 gene 1 | | ☑ |
| 60 | 192 | 18.1 | | 0.9 | 0.7 | 11 | Hsa.2208 | M67454 gene 1 | | |
| 61 | 190 | -12.6 | | 0.9 | 0.45 | | Hsa.2729 | V00511 gene 1 | | |
| 62 | 189 | -6.86 | | 0.91 | 0.45 | | Hsa.2947 | X54936 gene 1 | | |
| 63 | 183 | -20.9 | | 1 | 0.5 | | Hsa.2947 | X54936 gene 1 | | |
| 64 | 182 | 20.9 | | 0.94 | 0.76 | 9 | Hsa.1870 | M79463 gene 1 | | |

| | | | | | |
|---|---|---|---|---|---|
| 65 | 180 | 27.7 | 0.9 | 0.6 | 6 Hsa.36694 | D25217 gene 1 | □ | □ |
| 66 | 178 | -77.8 | 0.89 | 0.22 | Hsa.772 | M38451 gene 1 | □ | □ |
| 67 | 178 | -39.7 | 0.9 | 0.38 | Hsa.2402 | L36069 gene 1 | □ | □ |
| 68 | 176 | -249 | 0.85 | 0.35 | Hsa.967 | M33388 gene 1 | ☑ | □ |
| 69 | 175 | -4.32 | 0.95 | 0.45 | Hsa.837 | M13755 gene 1 | □ | □ |
| 70 | 165 | 20.7 | 1 | 0.76 | 8 Hsa.37262 | R84974 3' UTR 2a | ☑ | □ |
| 71 | 165 | 30.1 | 0.95 | 0.7 | 5 Hsa.27577 | R48578 3' UTR 2a | ☑ | □ |
| 72 | 165 | 31.1 | 0.9 | 0.65 | 5 Hsa.25777 | R62459 3' UTR 2a | ☑ | □ |
| 73 | 163 | 25.6 | 0.8 | 0.7 | 6 Hsa.35954 | H26960 3' UTR 2a | ☑ | □ |
| 74 | 161 | -10.4 | 0.9 | 0.5 | Hsa.1842 | M94547 gene 1 | ☑ | □ |
| 75 | 157 | 8.9 | 0.95 | 0.6 | Hsa.218 | T64470 3' UTR 1 | ☑ | □ |
| 76 | 154 | 26.3 | 0.76 | 0.62 | 6 Hsa.19553 | T97948 3' UTR 2a | □ | □ |
| 77 | 147 | 6.01 | 0.95 | 0.65 | Hsa.1387 | U14631 gene 1 | □ | □ |
| 78 | 141 | 15.1 | 0.85 | 0.7 | 9 Hsa.2823 | L05072 gene 1 | ☑ | □ |
| 79 | 141 | 20 | 0.86 | 0.79 | 7 Hsa.2208 | M67454 gene 1 | □ | □ |
| 80 | 141 | 3.08 | 0.95 | 0.65 | Hsa.955 | M32011 gene 1 | ☑ | ☑ |
| 81 | 140 | 10.1 | 1 | 0.48 | 14 Hsa.3279 | U28249 gene 1 | □ | □ |
| 82 | 136 | 7.45 | 0.95 | 0.71 | Hsa.9537 | U28369 gene 1 | ☑ | □ |
| 83 | 132 | 6.17 | 0.81 | 0.48 | Hsa.1846 | M96980 gene 1 | ☑ | □ |
| 84 | 119 | -8.34 | 0.88 | 0.76 | Hsa.36766 | H40980 3' UTR 2a | ☑ | □ |
| 85 | 118 | -6.81 | 0.8 | 0.6 | Hsa.1221 | T60155 3' UTR 1 | □ | □ |
| 86 | 117 | 12.3 | 0.9 | 0.6 | 10 Hsa.2826 | X07876 gene 1 | □ | □ |

FIG. 1G

| Gene Description | Induced |
|---|---|
| 52065 GROWTH ARREST AND DNA-DAMAGE-INDUCIBLE PROTEIN GADD45 (Homo sapiens) | |
| Human steroidogenic acute regulatory protein (StAR) mRNA, complete cds. | |
| LYSYL HYDROXYLASE (PLOD). (HUMAN) | |
| 151767 FASL RECEPTOR PRECURSOR (Homo sapiens) | |
| Homo sapiens creatine transporter mRNA, complete cds. | |
| KERATIN, TYPE I CYTOSKELETAL 15 (HUMAN);contains MER20 repetitive element ;. | |
| Human mRNA for thyroperoxidase. | |
| 275040 HEPATOCYTE GROWTH FACTOR-LIKE PROTEIN PRECURSOR (HUMAN);. | |
| 121731 CYTOCHROME P450 IVB1 (Rattus norvegicus) | |
| Homo sapiens dopamine transporter (SLC6A3) mRNA, complete cds. | |
| 139080 COMPLEMENT DECAY-ACCELERATING FACTOR 1 PRECURSOR (Homo sapiens) | |
| H sapiens mRNA for caveolin. | |
| Human endogenous retrovirus type C oncovirus sequence. | |
| 31481 TYROSINE-PROTEIN KINASE HCK (Homo sapiens) | |
| Homo sapiens ribosomal protein S6 kinase 2 (RPS6KA2) mRNA, complete cds. | |
| Human keratinocyte lectin 14 (HKL-14) mRNA, complete cds. | |
| Human Fas antigen (fas) mRNA, complete cds. | |
| Human mRNA encoding pregastrin (a regulatory hormone of gastric acid secretion and growth of the gastrointestinal mucosa). | |
| H.sapiens mRNA for placenta growth factor (PIGF). | |
| H.sapiens mRNA for placenta growth factor (PIGF). | |
| Human PML-2 mRNA, complete CDS. | |

| |
|---|
| Human mRNA (KIAA0027) for ORF, partial cds. |
| Human placenta-specific growth hormone mRNA, complete cds. |
| Human high conductance inward rectifier potassium channel alpha subunit mRNA, complete cds. |
| Human cytochrome P450 IID6 (CYP2D6) gene, complete cds. |
| INTERFERON-INDUCED 17 KD/ 15 KD PROTEIN (HUMAN) |
| 180447 FIBROBLAST GROWTH FACTOR RECEPTOR 3 PRECURSOR (Homo sapiens) |
| 153585 EBNA-2 NUCLEAR PROTEIN (Epstein-barr virus) |
| 36678 TROPONIN C, ISOFORM 2 (Balanus nubilis) |
| 182125 HDL-BINDING PROTEIN |
| HUMMLC2At; Homo sapiens; 593 base-pairs |
| 80486 LIVER CARBOXYLESTERASE PRECURSOR (HUMAN); |
| 121916 NEUTRAL CALPONIN, SMOOTH MUSCLE (Sus scrofa) |
| Human 11 beta-hydroxysteroid dehydrogenase type II mRNA, complete cds. |
| Homo sapiens interferon regulatory factor 1 gene, complete cds. |
| Human Fas antigen (fas) mRNA, complete cds. |
| NEUTROPHIL OXIDASE FACTOR (p67 PHOX) (HUMAN) |
| Human 11kd protein mRNA, complete cds. |
| Human semaphorin V mRNA, complete cds. |
| MYELIN TRANSCRIPTION FACTOR 1 (HUMAN); |
| 175991 NEURONAL CALCIUM SENSOR 1 (Rattus norvegicus) |
| 81422 HUMAN SMOOTH MUSCLE ALPHA-ACTIN (AORTIC TYPE) |
| Human mRNA for irp protein (int-1 related protein). |

FIG. 1I

| Gene # | Intensity in EB 1 | Intensity in EB | PM > MM in EB 1 | PM > MM in EB | Induced Ratio | EST # | Accession # | EST? | SAGE? |
|---|---|---|---|---|---|---|---|---|---|
| 87 | 117 | 1.9 | 0.92 | | 0.5 | Hsa.2208 | M67454 gene 1 | ☐ | ☐ |
| 88 | 107 | -21.3 | 0.8 | | 0.45 | Hsa.1881 | M14083 gene 1 | ☐ | ☐ |
| 89 | 107 | -0.81 | 0.8 | | 0.55 | Hsa.22529 | R37128 3' UTR 2a | ☑ | ☐ |
| 90 | 106 | 0.0333 | 1 | | 0.5 | Hsa.10171 | R70008 3' UTR 2a | ☑ | ☐ |
| 91 | 105 | 8.36 | 0.85 | | 0.7 | Hsa.2325 | U14747 gene 1 | ☐ | ☐ |
| 92 | 105 | -6.04 | 0.9 | | 0.38 | Hsa.2980 | X77737 gene 1 | ☐ | ☐ |
| 93 | 104 | 14.7 | 0.9 | | 0.7 | 7 Hsa.2131 | L25541 gene 1 | ☐ | ☐ |
| 94 | 103 | -168 | 0.87 | | 0.47 | Hsa.967 | M33388 gene 1 | ☐ | ☐ |
| 95 | 89 | -5.05 | 0.9 | | 0.6 | Hsa.1497 | M75126 | ☐ | ☐ |
| 96 | 85.9 | 6.79 | 0.81 | | 0.57 | Hsa.2013 | Z12020 gene 1 | ☐ | ☐ |
| 97 | 84.6 | 11.9 | 0.9 | | 0.65 | 7 Hsa.101 | D12620 gene 1 | ☐ | ☐ |
| 98 | 82.8 | 2.73 | 0.95 | | 0.5 | Hsa.1984 | J05200 gene 1 | ☑ | ☐ |
| 99 | 81.5 | 11.1 | 0.85 | | 0.65 | 7 Hsa.27854 | R51856 3' UTR 2a | ☑ | ☐ |
| 100 | 79.9 | -0.934 | 0.9 | | 0.45 | Hsa.20474 | R01072 3' UTR 2a | ☑ | ☐ |

FIG. 1J

| Gene Description: Induced |
|---|
| Human Fas antigen (fas) mRNA, complete cds. |
| Human beta-migrating plasminogen activator inhibitor I mRNA, 3' end. |
| 26063 COMPLEMENT C4 PRECURSOR (Homo sapiens) |
| 142450 VASCULAR ENDOTHELIAL GROWTH FACTOR PRECURSOR (Rattus norvegicus) |
| Human visinin-like peptide 1 homolog mRNA, complete cds. |
| H.sapiens mRNA for red cell anion exchanger (EPB3, AE1, Band 3) 3' non-coding region. |
| Human laminin S B3 chain (LAMB3) mRNA, complete cds |
| Human cytochrome P450 IID6 (CYP2D6) gene, complete cds. |
| Human hexokinase 1 (HK1) mRNA, complete cds. |
| Human mRNA for the MDM2 gene. |
| Human mRNA for cytochrome P-450LTBV. |
| RYANODINE RECEPTOR, SKELETAL MUSCLE (HUMAN);. |
| 39052 POTASSIUM CHANNEL PROTEIN EAG (Drosophila melanogaster) |
| 124416 SERINE THREONINE-PROTEIN KINASE COT-1 (Neurospora crassa) |

FIG. 2A

Repressed

| Gene # | Intensity in EB 1 | Intensity in EB | PM>MM in EB 1 | PM>MM in EB | Ratio | EST # | Accession # | EST? | SAGE? |
|---|---|---|---|---|---|---|---|---|---|
| 1 | 400 | 2750 | 0.95 | 1 | 6.9 | Hsa.1137 | T57686 3' UTR 1 | ☑ | ☑ |
| 2 | 323 | 2600 | 0.75 | 1 | 8.04 | Hsa.10770 | T76971 3' UTR 1 | ☐ | ☑ |
| 3 | 411 | 2300 | 1 | 1 | 5.59 | Hsa.1047 | R84411 3' UTR 1 | ☑ | ☑ |
| 4 | 261 | 2010 | 0.75 | 0.85 | 7.7 | Hsa.2715 | H77597 3' UTR 1 | ☐ | ☑ |
| 5 | 156 | 1970 | 0.95 | 1 | 12.7 | Hsa.14842 | T90759 3' UTR 2a | ☑ | ☑ |
| 6 | 303 | 1770 | 1 | 1 | 5.83 | Hsa.18397 | R81812 3' UTR 2a | ☑ | ☑ |
| 7 | 209 | 1580 | 0.85 | 1 | 7.57 | Hsa.1311 | R91912 3' UTR 1 | ☑ | ☐ |
| 8 | 311 | 1570 | 0.95 | 1 | 5.05 | Hsa.1205 | R08183 3' UTR 1 | ☑ | ☐ |
| 9 | 245 | 1460 | 0.95 | 1 | 5.95 | Hsa.2806 | X77956 gene 1 | ☐ | ☐ |
| 10 | 253 | 1450 | 0.75 | 0.95 | 5.75 | Hsa.11673 | H23544 3' UTR 2a | ☑ | ☐ |
| 11 | 246 | 1410 | 0.9 | 1 | 5.73 | Hsa.1190 | T74556 3' UTR 1 | ☑ | ☐ |
| 12 | 62 | 1350 | 0.9 | 1 | 21.8 | Hsa.1505 | M12623 gene 1 | ☐ | ☐ |
| 13 | 201 | 1170 | 0.8 | 1 | 5.84 | Hsa.1896 | J04173 gene 1 | ☑ | ☐ |
| 14 | 178 | 1110 | 0.9 | 1 | 6.23 | Hsa.122 | D14696 gene 1 | ☑ | ☐ |
| 15 | 176 | 1100 | 0.9 | 1 | 6.24 | Hsa.17649 | T87527 3' UTR 2a | ☑ | ☐ |
| 16 | 183 | 1060 | 0.9 | 1 | 5.8 | Hsa.1013 | T61661 3' UTR 1 | ☑ | ☐ |
| 17 | 102 | 1030 | 0.7 | 0.95 | 10.1 | Hsa.1401 | R02151 3' UTR 1 | ☑ | ☐ |
| 18 | 120 | 1020 | 0.9 | 1 | 8.48 | Hsa.18401 | R23889 3' UTR 2a | ☑ | ☐ |
| 19 | 96.4 | 999 | 0.85 | 1 | 10.4 | Hsa.1676 | H73758 3' UTR 1 | ☑ | ☐ |
| 20 | 146 | 876 | 0.85 | 1 | 5.99 | Hsa.1617 | D43950 gene 1 | ☐ | ☐ |
| 21 | 3.17 | 867 | 0.5 | 0.95 |  | Hsa.115 | D14657 gene 1 | ☐ | ☐ |

| | | | | | | | |
|---|---|---|---|---|---|---|---|
| 22 | 154 | 804 | 0.7 | 0.95 | 5.22 | Hsa.12893 | H49652 3' UTR 2a | ☐ |
| 23 | 105 | 632 | 0.95 | 1 | 6.04 | Hsa.1043 | M29065 gene 1 | ☐ |
| 24 | 64.5 | 602 | 0.75 | 0.8 | 9.34 | Hsa.448 | H09351 3' UTR 1 | ☑ |
| 25 | 61.4 | 556 | 0.6 | 1 | 9.05 | Hsa.6472 | T56604 3' UTR 2a | ☑ |
| 26 | 48.7 | 525 | 0.7 | 1 | 10.8 | Hsa.1778 | J04977 gene 1 | ☐ |
| 27 | 26.4 | 495 | 0.65 | 0.9 | 18.8 | Hsa.2965 | Y00705 gene 1 | ☐ |
| 28 | 37.3 | 491 | 0.75 | 0.95 | 13.2 | Hsa.1422 | M13450 gene 1 | ☑ |
| 29 | 93.9 | 487 | 0.85 | 1 | 5.19 | Hsa.1046 | H29485 3' UTR 1 | ☐ |
| 30 | 93.6 | 486 | 0.85 | 0.95 | 5.2 | Hsa.3037 | X74104 gene 1 | ☑ |
| 31 | 57.1 | 468 | 0.7 | 0.85 | 8.19 | Hsa.10011 | R06239 3' UTR 2a | ☑ |
| 32 | 84.5 | 456 | 0.85 | 0.95 | 5.4 | Hsa.347 | D16111 gene 1 | ☐ |
| 33 | 66 | 444 | 0.71 | 1 | 6.73 | Hsa.9937 | T94834 3' UTR 2a | ☑ |
| 34 | 54.8 | 423 | 0.76 | 0.86 | 7.72 | Hsa.3253 | U14603 gene 1 | ☐ |
| 35 | 26.7 | 414 | 0.8 | 1 | 15.5 | Hsa.1786 | L25941 gene 1 | ☑ |
| 36 | 48.4 | 403 | 0.8 | 1 | 8.31 | Hsa.14831 | H29320 3' UTR 2a | ☐ |
| 37 | 45.8 | 400 | 0.8 | 0.85 | 8.74 | Hsa.1606 | X64330 gene 1 | ☐ |
| 38 | 62 | 395 | 0.9 | 0.95 | 6.37 | Hsa.116 | D14658 gene 1 | ☑ |
| 39 | 62.4 | 391 | 0.86 | 0.86 | 6.27 | Hsa.3318 | H65116 3' UTR 1 | ☑ |
| 40 | 4.31 | 364 | 0.55 | 0.95 | | Hsa.13508 | R37660 3' UTR 2a | ☐ |
| 41 | 66.9 | 351 | 0.8 | 1 | 5.25 | Hsa.2959 | X74330 gene 1 | ☐ |
| 42 | 12.1 | 327 | 0.52 | 0.9 | 27 | Hsa.1343 | M13665 gene 1 | ☐ |
| 43 | 44.4 | 313 | 0.59 | 0.88 | 7.05 | Hsa.2459 | U10116 gene 1 | ☐ |

FIG. 2C

| Gene Description | Repressed |
|---|---|
| 79398 TUBULIN ALPHA-1 CHAIN (HUMAN). | |
| 113739 H.sapiens mRNA for metallothionein (HUMAN). | |
| 194660 SMALL NUCLEAR RIBONUCLEOPROTEIN ASSOCIATED PROTEINS B AND B' (HUMAN);. | |
| 214162 H.sapiens mRNA for metallothionein (HUMAN);. | |
| 111435 TUBULIN ALPHA-1 CHAIN (Gallus gallus) | |
| HUMAN mRNA FOR ADENOCARCINOMA-ASSOCIATED ANTIGEN (KSA), or GA733-2 | |
| 196105 PLACENTAL CALCIUM-BINDING PROTEIN (HUMAN);. | |
| 127228 HEAT SHOCK PROTEIN, CHAPERONIN 10, or GroES; MITOCHONDRIAL;. | |
| H.sapiens Id1 mRNA. | |
| 51894 GTP-BINDING NUCLEAR PROTEIN RAN (Homo sapiens) | |
| 84680 ATP SYNTHASE ALPHA CHAIN, MITOCHONDRIAL PRECURSOR (HUMAN);. | |
| Human non-histone chromosomal protein HMG-17 mRNA, complete cds. | |
| PHOSPHOGLYCERATE MUTASE, BRAIN FORM (HUMAN). | |
| Human mRNA (KIAA0108) for ORF (complete cds) and HepG2 mRNA identical sequence. | |
| 115413 HEAT SHOCK PROTEIN HSP 84 (Mus musculus). | |
| 78161 PROFILIN I (HUMAN) | |
| 124693 RAT mRNA for PROTEASOME SUBUNIT RC10-II, or HUMAN PROTEASOME SUBUNIT HSC10-II. | |
| 131036 TRANSFERRIN RECEPTOR PROTEIN (Homo sapiens) | |
| 214923 PSORIASIS-ASSOCIATED FATTY ACID BINDING PROTEIN HOMOLOG (HUMAN);. | |
| Human mRNA (KIAA0098) for ORF (human counterpart of mouse chaperonin containing TCP-1 gene), partial cds. | |
| Human mRNA for ORF(KIAA0101), comlpete cds. | |

| |
|---|
| 274422 ATPASE INHIBITOR, MITOCHONDRIAL (BOVIN). |
| Human hnRNP A2 protein mRNA. |
| 46019 MCM3 HOMOLOG (HUMAN);. |
| 73143 TUBULIN BETA-1 CHAIN (Haliotis discus) |
| Human Ku autoimmune antigen gene, complete cds. |
| Homo sapiens pstl mRNA for pancreatic secretory inhibitor (expressed in neoplastic tissue). |
| Human esterase D mRNA, 3'end. |
| 49970 LUPUS LA PROTEIN (HUMAN);. |
| H.sapiens mRNA for TRAP beta subunit. |
| 125446 TRANSCRIPTION INITIATION FACTOR TFIID (Homo sapiens) |
| Human mRNA for human homologue of rat phosphatidylethanolamine binding protein, complete cds. |
| 120041 HLA-DR ASSOC. PROTEIN I, P31 (also called Ii, In, M1, Dr gamma, XM 1) (Homo sapiens) |
| Human protein-tyrosine phosphatase (HU-PP-1) mRNA, partial sequence. |
| Homo sapiens integral nuclear envelope inner membrane protein (LBR) gene, complete cds. |
| 52626 HYPOTHETICAL GTP-BINDING PROTEIN IN PMI40-PAC2 INTERGENIC REGION (Saccharomyces cerevisiae) |
| H.sapiens mRNA for ATP-citrate lyase. |
| Human mRNA for ORF (KIAA0102), complete cds. |
| 238612 Human bumetanide-sensitive Na-K-Cl cotransporter (NKCC1 or BSC2) mRNA, complete cds. |
| 26573 STATHMIN (Homo sapiens) |
| H.sapiens mRNA for DNA primase (subunit p48). |
| Human c-myb mRNA, 3'end. |
| Human superoxide dismutase (SOD3 or EC-SOD) gene, complete cds. |

FIG. 2E

| Gene # | Intensity in EB 1 | Intensity in EB | PM > MM in EB 1 | PM > MM in EB | Repressed Ratio | EST # | Accession # | EST? | SAGE? |
|---|---|---|---|---|---|---|---|---|---|
| 44 | 47.1 | 303 | 0.75 | 1 | 6.44 | Hsa.1511 | V00530 gene 1 | ☐ | ☐ |
| 45 | 52.4 | 299 | 0.8 | 0.95 | 5.7 | Hsa.1067 | J04543 gene 1 | ☐ | ☐ |
| 46 | 50.1 | 296 | 0.75 | 1 | 5.91 | Hsa.1877 | M88108 gene 1 | ☐ | ☐ |
| 47 | 55.1 | 294 | 0.71 | 0.9 | 5.33 | Hsa.421 | D16294 gene 1 | ☐ | ☐ |
| 48 | 38.8 | 290 | 0.7 | 0.95 | 7.48 | Hsa.1583 | D42084 gene 1 | ☐ | ☐ |
| 49 | -49.3 | 287 | 0.62 | 0.86 |  | Hsa.1625 | H59259 3' UTR 1 | ☑ | ☐ |
| 50 | 54.3 | 280 | 0.76 | 1 | 5.16 | Hsa.3075 | X78627 gene 1 | ☐ | ☐ |
| 51 | 43.1 | 271 | 0.7 | 0.95 | 6.3 | Hsa.18494 | T93518 3' UTR 2a | ☑ | ☐ |
| 52 | 19.9 | 264 | 0.55 | 0.85 | 13.3 | Hsa.1573 | D42041 gene 1 | ☐ | ☐ |
| 53 | 46.5 | 262 | 0.65 | 0.94 | 5.64 | Hsa.2490 | D21262 gene 1 | ☐ | ☐ |
| 54 | 22.1 | 261 | 0.67 | 0.9 | 11.8 | Hsa.1595 | L32866 gene 1 | ☐ | ☐ |
| 55 | 26.1 | 253 | 0.76 | 0.95 | 9.67 | Hsa.1816 | T91855 3' UTR 1 | ☑ | ☐ |
| 56 | 10.2 | 251 | 0.65 | 0.8 | 24.6 | Hsa.1490 | R56440 3' UTR 1 | ☑ | ☐ |
| 57 | 29.9 | 250 | 0.65 | 0.95 | 8.34 | Hsa.9856 | R60195 3' UTR 2a | ☑ | ☐ |
| 58 | 10.4 | 248 | 0.65 | 1 | 23.9 | Hsa.150 | L10678 gene 1 | ☑ | ☐ |
| 59 | 40.2 | 245 | 0.95 | 0.85 | 6.09 | Hsa.7048 | R56401 3' UTR 2a | ☑ | ☐ |
| 60 | 6.69 | 242 | 0.57 | 0.95 |  | Hsa.1315 | D13639 gene 1 | ☐ | ☐ |
| 61 | 41.2 | 234 | 0.65 | 0.95 | 5.7 | Hsa.21993 | R12588 3' UTR 2a | ☑ | ☐ |
| 62 | 43.4 | 234 | 0.65 | 0.8 | 5.38 | Hsa.970 | M77836 gene 1 | ☑ | ☐ |
| 63 | 22.2 | 211 | 0.8 | 0.95 | 9.51 | Hsa.17935 | H01943 3' UTR 2a | ☑ | ☐ |
| 64 | 26.6 | 206 | 0.57 | 0.95 | 7.73 | Hsa.10122 | T52362 3' UTR 2a | ☑ | ☐ |
| 65 | 27.1 | 195 | 0.8 | 0.85 | 7.2 | Hsa.654 | L33930 gene 1 | ☐ | ☐ |

| | | | | | | |
|---|---|---|---|---|---|---|
| 66 | 27.2 | 195 | 0.7 | 0.9 | 7.18 | Hsa.10779 | X87212 gene 1 |
| 67 | 17 | 190 | 0.7 | 0.95 | 11.2 | Hsa.1815 | L31801 gene 1 |
| 68 | -4.22 | 189 | 0.6 | 0.8 | | Hsa.3091 | T49870 3' UTR 1 |
| 69 | 28.1 | 187 | 0.5 | 0.8 | 6.65 | Hsa.462 | U09564 gene 1 |
| 70 | 5.53 | 186 | 0.8 | 0.9 | | Hsa.42520 | H64001 3' UTR 2a |
| 71 | 21.6 | 175 | 0.6 | 0.8 | 8.09 | Hsa.1460 | M20867 gene 1 |
| 72 | 31.8 | 173 | 0.6 | 0.85 | 5.45 | Hsa.14771 | T70251 3' UTR 2a |
| 73 | 20.3 | 171 | 0.76 | 0.86 | 8.41 | Hsa.9868 | T50501 3' UTR 2a |
| 74 | 31.5 | 169 | 0.7 | 1 | 5.36 | Hsa.2892 | X76029 gene 1 |
| 75 | 17.7 | 168 | 0.67 | 0.9 | 9.49 | Hsa.1361 | M14219 gene 1 |
| 76 | 14.5 | 166 | 0.75 | 1 | 11.5 | Hsa.12976 | X74987 gene 1 |
| 77 | 27 | 164 | 0.55 | 0.9 | 6.06 | Hsa.2485 | D14694 gene 1 |
| 78 | -8.48 | 159 | 0.37 | 0.84 | | Hsa.234 | L19183 gene 1 |
| 79 | 30.9 | 157 | 0.8 | 0.9 | 5.09 | Hsa.1242 | T55008 3' UTR 1 |
| 80 | 15.8 | 147 | 0.7 | 0.95 | 9.33 | Hsa.25724 | R46716 3' UTR 2a |
| 81 | 28.6 | 145 | 0.7 | 0.85 | 5.07 | Hsa.38007 | R88418 3' UTR 2a |
| 82 | 28.5 | 145 | 0.65 | 0.9 | 5.09 | Hsa.1780 | R09502 3' UTR 1 |
| 83 | 23 | 145 | 0.7 | 0.95 | 6.29 | Hsa.1615 | D43948 gene 1 |
| 84 | 20.8 | 142 | 0.85 | 0.95 | 6.82 | Hsa.13795 | H00297 3' UTR 2a |
| 85 | 7.23 | 141 | 0.55 | 0.8 | | Hsa.1665 | L23959 gene 1 |
| 86 | 24.6 | 140 | 0.67 | 1 | 5.67 | Hsa.928 | M22538 gene 1 |

FIG. 2G

| Gene Description | Repressed |
|---|---|
| Human mRNA encoding IMP:pyrophosphate phosphoribosyltransferase E.C. 2.4.2.8. | |
| Human synexin mRNA, complete cds. | |
| Human p62 mRNA, complete cds. | |
| Human mRNA for mitochondrial 3-oxoacyl-CoA thiolase, complete cds. | |
| Human mRNA (KIAA0094) for ORF (yeast methionine aminopeptidase-related), partial cds. | |
| 204299 REPLICATION PROTEIN A 14 KD SUBUNIT (HUMAN); | |
| H.sapiens mRNA for translin. | |
| 117708 MYOSIN HEAVY CHAIN, CLONE 203 (Hydra attenuata) | |
| Human mRNA (KIAA0088) for ORF (alpha-glucosidase-related), partial cds. | |
| Human mRNA (KIAA0035) for ORF (rat 140kd nucleolar phosphoprotein homologue), partial cds. | |
| Human effector cell protease receptor-1 (EPR-1) gene, partial cds. | |
| 112020 C-1-TETRAHYDROFOLATE SYNTHASE, CYTOPLASMIC (HUMAN); | |
| 40874 TUBULIN GAMMA CHAIN (HUMAN); | |
| 42829 EUKARYOTIC INITIATION FACTOR 4B (Homo sapiens) | |
| PROFILIN II (HUMAN); | |
| 40753 RAN-SPECIFIC GTPASE-ACTIVATING PROTEIN, RanGAP (Homo sapiens) | |
| Human mRNA for ORF (KIAK0002), or HUMAN D-TYPE CYCLIN complete cds. | |
| 128385 HAMSTER RNA FOR CYCLIN B2 (mesocricetus auratus) | |
| PYRROLINE-5-CARBOXYLATE REDUCTASE (HUMAN); | |
| 150169 EUKARYOTIC INITIATION FACTOR 4E (Homo sapiens) | |
| 72050 NUCLEOTIDE-SENSITIVE CHLORIDE CHANNEL (Canis familiaris), or HUMAN CHLORIDE CHANNEL REGULATORY PROTEIN mRNA | |

| |
|---|
| Homo sapiens CD24 signal transducer mRNA, complete cds and 3' region. |
| H.sapiens mRNA for cathepsin C (dipeptidyl peptidase I). |
| Homo sapiens monocarboxylate transporter 1 (SLC16A1) mRNA, complete cds. |
| 68690 U1 SMALL NUCLEAR RIBONUCLEOPROTEIN A (HUMAN). |
| Human serine kinase (SRPK1) mRNA, complete cds. |
| 209484 CD9 ANTIGEN (Bos taurus), or HUMAN T245 PROTEIN |
| Human glutamate dehydrogenase (GDH) mRNA, complete cds. |
| 109334 NEGATIVE REGULATOR OF MITOSIS (Emericella nidulans) |
| 77138 EUKARYOTIC INITIATION FACTOR 1A (Sac cerevisiae), or HUMAN PROTEIN SYNTHESIS FACTOR 4C(eIF-4C) |
| H.sapiens mRNA for neuromedin U. |
| Human chondroitin/dermatan sulfate proteoglycan (PG40) core protein mRNA, complete cds. |
| H.sapiens mRNA for 2'-5' oligoadenylate binding protein. |
| Human mRNA (KIAA0024) for ORF (putative human counterpart of chinese hamster phosphatidylserine synthase gene), complete cds. |
| Human MAC30 mRNA, 3' end. |
| 74167 APOLIPOPROTEIN A-II PRECURSOR (HUMAN). |
| 36504 GTPASE ACTIVATING PROTEIN ROTUND (Drosophila melanogaster) |
| 166353 CLEAVAGE STIMULATION FACTOR, 50 KD SUBUNIT (Homo sapiens) |
| 127707 LAMININ BETA-1 CHAIN PRECURSOR (HUMAN);. |
| Human mRNA (KIAA0097) for ORF (novel protein), complete cds. |
| 149556 O-ANTIGEN POLYMERASE (Shigella flexneri) |
| Homo sapiens E2F-related transcription factor (DP-1) mRNA, complete cds. |
| NADH-UBIQUINONE DEHYDROGENASE 24 KD SUBUNIT PRECURSOR (HUMAN);. |

FIG. 2I

| Gene # | Intensity in EB 1 | Intensity in EB | PM > MM in EB 1 | PM > MM in EB | Ratio | EST # | Accession # | EST? | SAGE? |
|---|---|---|---|---|---|---|---|---|---|
| 87 | 27.1 | 139 | 0.8 | 0.9 | 5.14 | Hsa.1811 | M37510 gene 1 | | |
| 88 | 17.2 | 137 | 0.4 | 0.9 | 7.95 | Hsa.6633 | R61359 3' UTR 2a | ☑ | |
| 89 | 20.8 | 136 | 0.4 | 0.9 | 6.55 | Hsa.13172 | T73788 3' UTR 2a | ☑ | |
| 90 | 19.7 | 135 | 0.65 | 0.85 | 6.85 | Hsa.1423 | J04102 gene 1 | | |
| 91 | 18.1 | 134 | 0.57 | 0.9 | 7.41 | Hsa.13967 | T66747 3' UTR 2a | ☑ | |
| 92 | 19.2 | 134 | 0.7 | 1 | 6.96 | Hsa.1245 | M21154 gene 1 | ☑ | |
| 93 | 7.16 | 132 | 0.71 | 1 | | Hsa.13508 | R37660 3' UTR 2a | ☑ | |
| 94 | -0.0563 | 130 | 0.65 | 0.85 | | Hsa.28663 | H10045 3' UTR 2a | ☑ | |
| 95 | 6.27 | 129 | 0.55 | 0.95 | | Hsa.1200 | D38553 gene 1 | | |
| 96 | 8.89 | 128 | 0.67 | 0.9 | | Hsa.2070 | J04088 gene 1 | | |
| 97 | 1.42 | 124 | 0.7 | 0.9 | | Hsa.45678 | H88978 3' UTR 2a | ☑ | |
| 98 | 13.2 | 123 | 0.45 | 0.9 | 9.27 | Hsa.18077 | H02009 3' UTR 2a | | |
| 99 | 12.3 | 121 | 0.62 | 0.95 | 9.84 | Hsa.1219 | M16827 gene 1 | | |
| 100 | 10.9 | 119 | 0.5 | 0.9 | 11 | Hsa.1952 | T96666 3' UTR 1 | ☑ | |

FIG. 2J

| Gene Description — Repressed |
|---|
| Human methylmalonyl CoA mutase (MUT) gene, exon 13. |
| 37866 BASIGIN PRECURSOR (Gallus gallus) |
| 84443 GA BINDING PROTEIN BETA-1 CHAIN (Homo sapiens) |
| Human erythroblastosis virus oncogene homolog 2 (ets-2) mRNA, complete cds. |
| 53193 26S PROTEASE REGULATORY SUBUNIT 6 (Homo sapiens) |
| S-ADENOSYLMETHIONINE DECARBOXYLASE PROENZYME (HUMAN);. |
| 26573 STATHMIN (Homo sapiens) |
| 46827 VAV ONCOGENE (Homo sapiens) |
| Human mRNA (KIAA0074) for ORF (yeast C728 protein-related), partial cds. |
| Human DNA topoisomerase II gene (top2), gene 1 |
| Homo sapiens cDNA clone 253186 3' |
| 151010 EUKARYOTIC PEPTIDE CHAIN RELEASE FACTOR SUBUNIT 1 (Homo sapiens) |
| Human medium-chain acyl-CoA dehydrogenase (ACADM) mRNA, complete cds. |
| 121357 A49436 CDI1=CYCLIN-DEPENDENT KINASE INTERACTOR 1 -;. |

P53-REGULATED GENES

TECHNICAL FIELD OF THE INVENTION

The invention relates to the area of gene regulation, in particular the area of regulation of genes involved in tumorigenesis.

BACKGROUND OF THE INVENTION

P53 is the name of a human tumor suppressor gene and its protein product. About 55 percent of all human cancers from many cell or tissue types suffer mutations in both alleles of the p53 gene. People who have inherited such mutations, will develop cancer over their lifetimes.

The p53 protein is a transcription factor, which regulates the expression of a large number of genes. High levels of an active wild type p53 protein in a cell cause these genes to be transcribed at a high rate. Elucidation of the functions of some of these "p53-regulated or -inducible genes" informs the art of how the p53 protein protects humans from cancers.

There is a need in the art to discover p53-inducible genes and their functions, so that we may have a chance to circumvent the effects of p53 mutations in cancer, by activating the p53-inducible genes and repressing the p53-repressible genes, so as to arrest the cancer's growth. Thus, the elucidation of such p53-regulated genes provides useful and valuable information.

SUMMARY OF THE INVENTION

In one embodiment, a method is provided for diagnosing cancer or for determining p53 status in a sample suspected of being neoplastic. The level of expression of an RNA transcript or its translation product in a first sample of a first tissue is compared to the level of expression of the transcript or translation product in a second sample of a second tissue. The first tissue is suspected of being neoplastic and the second tissue is a normal human tissue. The first and second tissue are of the same tissue type. The transcript is a transcript of a gene selected from the group consisting of gene numbers 1–8, 10, 12, 14–58, 60–68, and 70–100, as shown in FIG. 1. The first sample is categorized as neoplastic or as having a mutant p53 when expression is found to be the same or lower in the first sample than in the second sample.

According to another embodiment a method is provided for diagnosing cancer or for determining p53 status in a sample suspected of being neoplastic. The level of expression of an RNA transcript or its translation product in a first sample of a first tissue is compared to the level of expression of the transcript or translation product in a second sample of a second tissue. The first tissue is suspected of being neoplastic and the second tissue is a normal human tissue. The first and second tissue are of the same tissue type. The transcript is a transcript of a gene selected from the group consisting of gene numbers 7–24, and 26–100 as shown in FIG. 2. The first sample is categorized as neoplastic or as having a mutant p53 when expression is found to be the same or higher in the first sample than in the second sample.

Another aspect of the invention is a method of diagnosing cancer or determining p53 status in a sample suspected of being neoplastic. The level of expression of at least one RNA transcript or its translation product in a first sample of a first tissue is compared to the level of expression of the transcripts or translation products in a second sample of a second tissue. The first tissue is suspected of being neoplastic and the second tissue is a normal human tissue. The first and second tissue are of the same tissue type. The first group of RNA transcripts consists of transcripts of genes selected from the group of genes numbered 1–8, 10, 12, 14–58, 60–68, and 70–100 as shown in FIG. 1. The second group of RNA transcripts consists of transcripts of genes selected from the group consisting of genes numbered 7–24, and 25–100 as shown in FIG. 2. The first sample is categorized as neoplastic or as having a mutant p53 when expression of at least one of the first group of RNA transcripts or translation products is found to be the same or lower in the first sample than in the second sample, and expression of at least one of the second group of transcripts or translation products is found to be the same or higher in the first sample than in the second sample.

According to another aspect of the invention a method is provided for evaluating carcinogenicity of an agent. A test agent is contacted with a human cell. The level of expression of at least one transcript or its translation product is determined in the human cell after contacting with the agent. The transcript is of a gene selected from the group consisting of genes numbered 1–8, 10, 12, 14–58, 60–68, and 70–100 in FIG. 1 and genes numbered 7–24, and 26–100 in FIG. 2. An agent which decreases the level of expression of a gene identified in FIG. 1, or an agent which increases the level of expression of a gene identified in FIG. 2 is identified as a potential carcinogen.

Another aspect of the invention is directed to a method of treating cancer in a patient. A polynucleotide is administered to cancer cells of a patient. The polynucleotide comprises a coding sequence of a gene selected from the group consisting of genes numbered 1–8, 10, 12, 14–58, 60–68, and 70–100 in FIG. 1. The cancer cells of the patient harbor a mutant p53 gene. As a result of the administration, the gene is expressed in cells of the cancer.

Yet another aspect of the invention is directed to a method of treating cancer in a patient. An antisense construct comprising at least 12 nucleotides of a coding sequence of a gene selected from the group consisting of genes numbered 7–24, and 26–100 in FIG. 2 is administered to cancer cells of a patient. The coding sequence is in 3' to 5' orientation with respect to a promoter which controls its expression. The cancer cells harbor a mutant p53 gene. As a result of the administration, an antisense RNA is expressed in cells of the cancer.

According to still another aspect of the invention a method is provided of screening for drugs useful in the treatment of cancer. A cell which harbors a p53 mutation is contacted with a test substance. Expression of a transcript or its translation product is monitored. The transcript is of a gene selected front the group consisting of genes numbered 1–8, 10, 12, 14–58, 60–68, and 70–100 in FIG. 1 and genes numbered 7–24, and 26–100 in FIG. 2. A test substance is identified as a potential drug for treating cancer if it increases expression of a gene as shown in FIG. 1 or decreases expression of a gene as shown in FIG. 2.

Another aspect of the invention is a method of screening for drugs useful in the treatment of cancer. A tumor cell which overexpresses MDM2 is contacted with a test substance. Expression of a transcript or its translation product is monitored. The transcript is of a gene selected from the group consisting of genes numbered 1–8, 10, 12, 14–58, 60–68, and 70–100 in FIG. 1 and genes numbered 7–24, and 26–100 in FIG. 2. A test substance is identified as a potential drug for treating cancer if it increases expression of a gene as shown in FIG. 1 or decreases expression of a gene as shown in FIG. 2.

Yet another aspect of the invention provides a set of at least two nucleotide probes which hybridize to a set of p53-regulated genes. The genes are selected from the group consisting of genes numbered 1–8, 10, 12, 14–58, 60–68, and 70–100 in FIG. 1 and genes numbered 7–24, and 26–100 in FIG. 2.

These and other embodiments of the invention provide the art with methods for diagnosis, treatment and drug discovery for cancers. In addition, it provides a convenient and rapid carcinogenicity test.

BRIEF DESCRIPTION OF THE DRAWINGS

FIG. 1 is a Table showing genes induced by p53. The column headings are as follows. "Eb1" denotes the cell line EB1-α, i.e., a cell line which contains a zinc-inducible p53 gene. "EB" denotes the cell line EB1, a cell line which has a p53 mutant gene that fails to produce or express detectable p53 protein. "PM" denotes the number of perfect match oligonucleotides for a gene which hybridized and "MM" denotes the number of mismatch oligonucleotides for a gene which hybridized. "Ratio" is the ratio of intensity of EB1-α to EB1. "Accession number" refers to a GenBank accession number. "EST?" if checked indicates that the function of the nucleic acid sequence has not been determined. "SAGE?" if checked indicates that analysis using the SAGE technique also detected this gene as p53-regulated. See http://welch.link.welchjhu.edu/~molgen-g/P53-SAGE.HTM. FIG. 2 is a Table showing genes repressed by p53. Column headings are the same as in FIG. 1.

DETAILED DESCRIPTION

It is a discovery of the present inventors that p53 regulates a whole host of genes, increasing and decreasing expression of their mRNA and protein products. These genes have not previously been identified as p53 regulated. In some cases the biological functions of the genes is unknown. However, the now-established regulation by p53 indicates that the genes are involved in progression and arrest of the cell cycle.

A sampling of 6800 human genes were tested for the effects of p53 expression on their expression. Such a massive screening permits the identification of many genes which were heretofore not known to be p53 regulated.

Genetic status of p53 alleles (mutant or wild-type) has been shown to correlate well with a neoplastic state. Thus diagnosis can be provided based on the status of p53 alleles of cells. The level of expression of an RNA transcript or its translation product can be determined using any techniques known in the art. Specific oligonucleotide probes for the relevant genes can be used in hybridization experiments, as is known in the art. Any hybridization format for determining specific RNA levels can be used, including but not limited to Northern blots, slot blots, dot blots, and hybridization to oligonucleotide arrays. Specificity of hybridization can be assessed by varying degrees of stringency of the hybridization conditions. In addition, comparison of mismatch to perfect match oligonucleotide probes can be used to determine specificity of binding. To assess specific translation product (protein) expression levels, antibodies specific for the protein can be used readily. Again, any format known in the art for measuring specific protein levels can be used, including sandwich assays, ELISAs, immunoprecipitations, and Western blots. Any of monoclonal antibodies, polyclonal antibodies, single chain antibodies, and antibody fragments may be used in such assays. Specificity of immunologic reactions can be assessed using competitor antibodies or proteins, as well as by varying the immunoreaction conditions. Monitoring expression product levels involves determining amounts of a specific expression product. Amounts determined need not be absolute amounts, but may be relative amounts determined under different conditions, for example, in the presence and absence of a test compound.

Probes according to the present invention may be labeled or unlabeled, tethered to another substance or in solution, synthetically made or isolated from nature. Probes can be nucleic acids, either RNA or DNA, which contain naturally occurring nucleotide bases or modified bases. The probes may contain normal nucleotide bonds or peptide bonds. Oligonucleotide probes may be of any length which provides meaningful specificity of hybridization. Thus probes may be as small as 10 nucleotides, and preferably they are between 12 and 30 nucleotides in length. However, oligonucleotide probes may be significantly longer, in the range of 30 to 100 nucleotides, 100 to 500 nucleotides or 500 to 2000 nucleotides. Probes may be attached to polymers, either soluble or non-soluble. Probes may be attached or bonded to solid substrates such as filters, sheets, chips, slides, and beads.

High density arrays are particularly useful for monitoring the expression control at the transcriptional, RNA processing and degradation level. The fabrication and application of high density arrays in gene expression monitoring have been disclosed previously in, for example, WO 97/10365, WO 92/10588, U.S. application Ser. No. 08/772,376 filed Dec. 23, 1996; Ser. No. 08/529,115 filed on Sep. 15, 1995; Ser. No. 08/168,904 filed Dec. 15, 1993; Ser. No. 07/624,114 filed on Dec. 6, 1990 now abandoned, Ser. No. 07/362,901 filed Jun. 7, 1990, now abandoned, all incorporated herein for all purposed by reference. In some embodiments using high density arrays, high density oligonucleotide arrays are synthesized using methods such as the Very Large Scale Immobilized Polymer Synthesis (VLSIPS) disclosed in U.S. Pat. No. 5,445,934 incorporated herein for all purposes by reference. Each oligonucleotide occupies a known location on a substrate. A nucleic acid target sample is hybridized with a high density array of oligonucleotides and then the amount of target nucleic acids hybridized to each probe in the array is quantified. One preferred quantifying method is to use confocal microscope and fluorescent labels. The GeneChip® system (Affymetrix, Santa Clara, Calif.) is particularly suitable for quantifying the hybridization; however, it will be apparent to those of skill in the art that any similar systems or other effectively equivalent detection methods can also be used.

Tissue samples which can be tested according to the present invention are any which are derived from a patient, whether human, other domestic animal, or veterinary animal. Vertebrate animals are preferred, such as mice, humans, horses, cows, dogs, and cats, although any organism for which p53 status can be determined may be used. The form of the samples may be any which are routinely used in the art for determining the amounts of specific proteins or mRNA molecules. The samples may be fixed or unfixed, homogenized, lysed, cryopreserved, etc. It is most desirable that matched tissue samples be used as controls. Thus, for example, a suspected colorectal cancer tissue will be compared to a normal colorectal epithelial tissue.

FIGS. 1 and 2 below show genes which are induced by p53 and repressed by p53, respectively. Genes which are identified with a check in the column headed "SAGE" are those which are believed to be previously identified as p53-regulated. Genes which are not checked are believed to be previously unknown as p53-regulated genes. Genes numbered 1–8, 10, 12, 14–58, 60–68, and 70–100 in FIG. 1, and genes numbered 7–24, and 26–100 in FIG. 2, are believed to be such previously unknown p53-regulated genes.

While assaying expression of any single one of the genes identified as p53-regulated may be useful for diagnosis and assays, it may be desirable to use larger sets to confirm the global cellular effects observed. In this regard, it may be desirable to assay for at least 2, 5, 10, 20, 30, 32, 50, 70, or 77 genes of one or both categories of regulation. It may be useful to use both induced and repressed genes to get such a global snapshot of gene regulation.

In a particularly preferred embodiment, oligonucleotide probes for RNA transcripts are attached to solid supports. Such supports are preferably arrays where nucleic acid molecules are attached to the substrate in predetermined positions. In one particular embodiment, the nucleic acid molecules are synthesized on the substrate. In another embodiment the nucleic acid molecules are applied to the solid support after synthesis or isolation.

Test samples for mRNA are typically harvested from the tissue samples and may be used directly or processed as follows. The sample mRNA is reverse transcribed using reverse transcriptase to form cDNA. A promoter is ligated to the cDNA at its 5', 3', or both ends. (5' and 3' refer to orientation on the coding strand of DNA.) If two promoters are used on one cDNA they can be the same or different. The cDNA is then used as a template to transcribe in vitro to form test mRNA. The test RNA can then be used to hybridize to nucleic acid molecules or probes, preferably on a solid support, more preferably on an oligonucleotide array. These processing steps are well known in the art.

The regulated genes discovered here can form the basis of a carcinogenicity test. Test agents are evaluated to see if their effects on human cells mimic the effects of loss of p53. Thus the agents are in essence being evaluated for the ability to induce a p53 mutation, or a mutation in another gene which is in the same regulatory pathway, or a non-genetic effect which mimics p53 loss. Test agents which are found to have at least some of the same constellation of effects as p53 loss on the regulation of the genes identified herein to be p53-regulated, are identified as potential carcinogens. Any single gene identified can be used, as can at least 2, 5, 10, 20, 30, 32, 40, 50, 70, 90, 100, 125, or 145 of the genes identified herein.

The genes identified herein as p53-induced can be delivered therapeutically to cancer cells. Antisense constructs of the genes identified herein a, p53-repressed can be delivered therapeutically to cancer cells. The goal of such therapy is to retard the growth rate of the cancer cells. Expression of the sense molecules and their translation products or expression of the antisense mRNA molecules has the effect of inhibiting the growth rate of cancer cells or inducing apoptosis (a radical reduction in the growth rate of a cell). Sense nucleic acid molecules are preferably delivered in constructs wherein a promoter is operatively linked to the coding sequence at the 5'-end and initiates transcription of the coding sequence. Anti-sense constructs contain a promoter operatively linked to the coding sequence at the 3'-end such that upon initiation of transcription at the promoter an RNA molecule is transcribed which is the complementary strand from the native mRNA molecule of the gene.

Delivery of nucleic acid molecules can be accomplished by many means known in the art. Gene delivery vehicles (GDVs) are available for delivery of polynucleotides to cells, tissue, or to a the mammal for expression. For example, a polynucleotide sequence of the invention can be administered either locally or systemically in a GDV. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated. The invention includes gene delivery vehicles capable of expressing the contemplated polynucleotides. The gene delivery vehicle is preferably a viral vector and, more preferably, a retroviral, adenoviral, adeno-associated viral (AAV), herpes viral, or alphavirus vectors. The viral vector can also be an astrovirus, coronavirus, orthomyxovirus, papovavirus, paramyxovirus, parvovirus, picornavirus, poxvirus, togavirus viral vector. See generally, Jolly, Cancer Gene Therapy 1:51–64 (1994); Kimura, Human Gene Therapy 5:845–852 (1994), Connelly, Human Gene Therapy 6:185–193 (1995), and Kaplitt, Nature Genetics 6:148–153 (1994).

Delivery of the gene therapy constructs of this invention into cells is not limited to the above mentioned viral vectors. Other delivery methods and media may be employed such as, for example, nucleic acid expression vectors, polycationic condensed DNA linked or unlinked to killed adenovirus alone, for example see Curiel, Hum Gene Ther 3:147–154 (1992) ligand linked DNA, for example, see Wu, J. Biol. Chem. 264:16985–16987 (1989), eucaryotic cell delivery vehicles cells, for example see U.S. Ser. No. 08/240,030, filed May 9, 1994, now abandoned and U.S. Ser. No. 08/404,796, filed Mar. 15, 1995, deposition of photopolymerized hydrogel materials, hand-held gene transfer particle gun, as described in U.S. Pat. No. 5,149,655, ionizing radiation as described in U.S. Pat. No. 5,206,152 and in PCT Patent Publication No. WO 92/11033, nucleic charge neutralization or fusion with cell membranes. Additional approaches are described in Philip, Mol. Cell. Biol. 14:2411–2418 (1994) and in Woffendin, Proc. Natl. Acad. Sci. 91:1581–585 (1994). Particle mediated gene transfer may be employed, for example see U.S. provisional application No. 60/023,867. Briefly, the sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, as described in Wu and Wu, J. Biol. Chem. 262:4429–4432 (1987), insulin as described in Hucked, Biochem. Pharmacol. 40:253–263 (1990), galactose as described in Plank, Bioconjugate Chem 3:533–539 (1992), lactose or transferrin. Naked DNA may also be employed. Exemplary naked DNA introduction methods are described in PCT Patent Publication No. WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Patent Publication Nos. WO 95/13796, WO 94/23697, and WO 91/144445, and EP No. 524,968.

Drugs useful in the treatment of cancer can be screened and identified using the p53-regulated genes disclosed herein. Cells of two types can be contacted with test substances. The cells may not carry a wild-type p53 allele or the cells may overexpress the MDM2 gene product. MDM2 sequesters wild-type p53. Therefore MDM2-overexpressing cells mimic cells which are genetically deficient for p53.

Expression of one or more of the p53-regulated genes of the present invention is monitored in the presence of the test substance. A test substance which mimics one or more of the regulatory effects of p53 on the p53-regulated genes is a potential therapeutic agent for treating cancer. Such agents can be subsequently tested in any number of other assays to determine their ultimate usefulness as a drug.

Sets of at least two oligonucleotide probes are provided. Preferably the probes are exclusively perfectly matched probes to the genes. However, mismatch probes having less than 5% mismatched nucleotides can be used. The probes hybridize to the p53-regulated genes disclosed herein in FIGS. 1 and 2. Particularly useful genes are those numbered 1–8, 10, 12, 14–58, 60–68, and 70–100 in FIG. 1, and those numbered 7–24, and 26–100 in FIG. 2. It is preferred that all of the oligonucleotide probes hybridize to p53-regulated genes, although it is permissible to have probes for other genes present which are not p53 regulated. Preferably the probes for other genes comprise less than 50% of the probes, and more preferably comprise less than 25%, 15%, 10%, 5%, 2%, or 1%. The sets of p53 regulated genes may comprise at least five, ten, fifteen, twenty, twenty-five, thirty, fifty, seventy-five, 100, or 140 oligonucleotide probes p53-regulated genes, as disclosed herein. The probes may be attached to a polymer, soluble or insoluble, naturally occurring or synthetic. The probes may be attached to a solid support, in a gel matrix, or in solution. The probes may be individually packaged and contained within a single container, or may be mixed in one or more mixtures. Preferably the probes are arrayed on a solid support.

The above disclosure generally describes the present invention. A more complete understanding can be obtained by reference to the following specific examples which are provided herein for purposes of illustration only, and are not intended to limit the scope of the invention. The following methods were used in the examples reported below.

EXAMPLE

Eb-1 cells were derived from a human colon carcinoma and these cells have a p53 mutant gene that fails to produce or express detectable p53 protein. A p53 wild-type gene was inserted into these cells under the regulation of a metallothionein (MT) promoter. In the presence of zinc, this promoter expresses the p53 gene but in the absence (or low levels) of zinc, little or no p53 mRNA or protein are produced. Thus, p53 mRNA and protein are zinc-inducible and the p53-regulated genes are similarly induced by the addition of zinc. The Eb-1 cells (original cell line) without a p53 inducible wild-type gene are called Eb-1 and Eb-1 cells with the MT-p53 inducible gene are termed Eb-1 ($\alpha$).

Eb-1 cells and Eb-1 (alpha) cells were grown in culture and either left untreated or exposed to zinc. Four hours and ten hours after the addition of zinc, these cells were harvested for analysis.

The messenger RNA was extracted from these cells and purified. An oligo-dT primer was used to produce a reverse transcriptase copy of the mRNA and then, an oligonucleotide linker was ligated to the end of the cDNA where the linker has a T-7 promoter sequence incorporated into it. All of the cDNAs were cloned into vectors, which were then employed to make mRNA copies in vitro using the T-7 RNA polymerase and fluorescent biotinylated nucleotides. The RNA products were hydrolyzed to an average size of 50 nucleotides in length.

The hydrolyzed RNA was hybridized to a chip that contains deoxyoligonucleotide sequence (25 in length) that derive from a database of 6,800 known genes or EST sequences. There is a 20-fold redundancy for each gene or EST sequence and for each perfect sequence match, a mismatched sequence (one base different in the middle of the sequence of 25 nucleotides).

After a short hybridization, that measures the rate (amount) of fluorescent probe hybridized to each set of 20 oligonucleotide sequences, the chips are washed and read by a digital confocal microscope to quantitate the intensity of the fluorescent readout. Gene expression or mRNA concentration is measured by changes in the fluorescent readout for probe pairs. The specificity of the measurements is given by the ratio of hybridization to a perfect sequence matched probe compared with the hybridization to a mismatched probe.

For this experiment a control was run; Eb-1 cells treated or untreated with zinc. Here no p53 cDNA was present so the only variable was the exposure of the cells to zinc. Out of all the genes or sequences tested in these cells (6,800), only six changed their gene expression patterns in response to added zinc and five (1–5) of these six genes are under the control of zinc and cadmium inducible promoters. This experiment serves as an excellent control for the p53 regulation of genes.

For the experiment, Eb-1 ($\alpha$) cells were treated with zinc or left untreated and at four or ten hours, the cells were harvested. RNA was prepared and processed as described above. The hybridization to the 6,800 different oligonucleotide sequences on the chip (each cDNA had a twenty-fold sequence redundancy covering different sequences in the cDNA) was carried out and the analysis of the data was done by an algorithm. The following criteria were employed to accept a gene as p53-inducible or repressed by p53: (1) the relative intensity of the mRNA hybridization level of an induced gene or a decrease with a repressed gene, was above 160 relative units; this has been shown to be a reproducible level with minimal statistical fluctuations; (2) the fraction of probe pairs (matched hybridized and mismatch not hybridized) had to be 0.85 or greater (17 out of 20 perfect matches); (3) the ratio of induction by p53 or repression by p53, when comparing cellular RNA from Eb-1 zinc-induced cells, was five-fold or greater. Thus, only genes whose mRNA levels increased five-fold or decreased five-fold from a high baseline are reported by this analysis.

Of 6,800 cDNAs detectable on the chip, 70 genes were induced by p53 and 77 were repressed by p53. Once again, there were excellent positive controls in this experiment. The known p53 inducible genes such as p21-WAF-1, IGF-BP-3, MDM-2, GAD-45, as well as some recently reported 53 inducible genes (PIIGS) were detected by this chip hybridization. Similarly, a repressed gene, MAP-4 previously reported in the literature was repressed after p53 induction in Eb-1($\alpha$) cells as detected in this experiment.

FIG. 1 lists the genes which are induced by p53 and FIG. 2 lists the genes which are repressed by p53.

We claim:

1. A method of screening to identify test substances which induce or repress expression of genes which are induced or repressed by p53, comprising:

contacting a cell which harbors a p53 mutation with a test substance;

monitoring expression of a transcript or its translation product, wherein the transcript specifically hybridizes to a gene selected from a first and a second group, wherein the first group consists of IG GAMMA-1 CHAIN C REGION (HUMAN), Human 1 g gamma3 heavy chain disease OMM protein mRNA, 274912 MYELIN TRANSCRIPTION FACTOR 1 (*Homo sapiens*), 152524 CYCLIN-DEPENDENT KINASE INHIBITOR 1 (*Homo sapiens*), *H. sapiens* mRNA for 43 kDa inositol polyphosphate 5-phosphatase, Human N-acetylgalactosamine 6-sulphatase (GALNS) gene, exon 14, 155730 KERATIN, TYPE I CYTOSKELETAL 17 (HUMAN), *H. sapiens* mRNA (clone 9112), kinase related protein, Human placental cDNA coding for 5'nucleotidase (EC 3.1.3.5), *H. sapiens* MLN62 mRNA, Human activated p21cdc42Hs kinase (ack) mRNA, complete cds., 81780 COMPLEMENT C4 PRECURSOR (*Homo sapiens*), 172486 clone, mRNA for tuberin, or TSC2 gene, *Homo sapiens* of cardiac alpha-myosin heavy chain gene, KERATIN, TYPE II CYTOSKELETAL 5 (HUMAN); contains MSR1 repetive element, 182000 FK506-BINDING PROTEIN PRECURSOR (*Mus musculus*), Human insulin-like growth factor-binding protein-3 gene, complete Cds, clone HL1006d, 72466 ALPHA CRYSTALLIN B CHAIN (HUMAN), *Homo sapiens* mRNA for serum response factor-related protein, RSRFR2, 198656 HEPATOCYTE GROWTH FACTOR-LIKE PROTEIN PRECURSOR (*Homo sapiens*), 62461 SMALL NUCELAR RIBONUCLE-ORPROTEIN Particle N (SNRPN), contains MSR1 repetive element, 155335 INTEGRIN ALPHA-3 (*Homo sapiens*), 41792 TUBULIN BETA-2 CHAIN (HUMAN), Human estradiol 17 beta-dehydrogenase gene, complete cds, *H. sapiens* mRNA for cystathionine-betasynthase, *Homo sapiens* of cardiac alpha-myosin heavy chain gene, Human mRNA for thyroglobulin, Human guanine nucleotide regulatory protein (ABR) mRNA, complete cds, Human novel growth factor receptor mRNA 3' Cds, 142899 DNA-DIRECTED RNA POLYMERASE III LARGEST SUBUNIT (*Plasmodium falciparum*), Human mRNA for collagen VI alpha-1 C-terminal globular domain, *Homo sapiens* sodium channel type I, beta subunit (SCN1B) mRNA, complete cds., 50887 GUANINE NUCLEOTIDE DISSOCIATION STIMULATOR RALGDSA (*Mus musculus*), Human cytochrome P450 4F2 (CYP4F2) mRNA, complete cds, Human MAGE-2 gene exons 1–4, complete cds, *H. sapiens* mRNA for transforming growth factor alpha, 38251 *H. sapiens* HSJ1 mRNA, p53, *H. sapiens* mRNA for intestine-specific annexin, KERATIN, TYPE ICY-TOSKELETAL 15 (HUMAN); contains MER20 repetitive element, 5065 GROWTH ARREST AND DNA-DAMAGE-INDUCIBLE PROTEIN GADD45 (*Homo sapien*), Human steroidogenic acute regulatory protein (StAR) mRNA, complete cds, LYSYL HYDROXYLASE (PLOD), (HUMAN), 151767 FASL RECEPTOR PRECURSOR (*Homo sapiens*), *Homo sapiens* creatine transporter mRNA, complete cds, KERATIN TYPE I CYTOSKELETAL 15 (HUMAN); contains MER20 repetitive element, Human mRNA for thyroperoxidase, 275040 HEPATOCYTE GROWTH FACTOR-LIKE PROTEIN PRECURSOR (HUMAN), 121731 CYTOCHROME P450 IVB1 (*Rattus norvegicus*), *Homo sapiens* dopamine transporter (SLC6A3) mRNA, complete cds, 139080 COMPLEMENT DECAY-ACCELERATING FACTOR 1 PRECURSOR (*Homo sapiens*), *H. sapiens* mRNA for caveolin, Human endogenoous retrovirus type C onc-covirus sequence, 31481 TYROSINE-PROTEIN KINASE HCK (*Homo sapiens*), *Homo sapiens* ribosomal protein S6 kinase 2 (RPS6KA2) mRNA, complete cds, Human Fas antigen (fas) mRNA, complete cds, Human mRNA encoding pregastrin (a regulatory hormone of gastric acid secretin and growth of the gastrointestinal mucosa), *H. sapiens* mRNA for placenta growth factor (PIGF), *H. sapiens* mRNA for placenta growth factor (PIGF), Human PML-2 mRNA, complete Cds, Human mRNA (KIAA0027) for ORF, partial cds, Human placenta-specific growth hormone mRNA, complete cds, Human high conductance inward rectifier potassium channel alpha subunit mRNA, complete cds, Human cytochrome P450 IID6 (CYP2D6) gene, complete cds, 180447 FIBROBLAST GROWTH FACTOR RECEPTOR 3 PRECURSOR (*Homo sapiens*), 153585 EBNA-2 NUCLEAR PROTEIN (Epstein-barr virus), 36678 TROPONIN C, ISOFORM 2 (*Balanus nubilis*), 182125 HDL-BINDING PROTEIN, HUMMLC2At; *Homo sapiens*: 593 base pairs, 80486 LIVER CARBOXYLESTERASE PRECURSOR (HUMAN), 121916 NEUTRAL CALPONIN, SMOOTH MUSCLE (*Sus scrofa*), Human 11 beta hydroxysteroid dehydrogenase type II mRNA, complete cds, *Homo sapiens* interferon regulatory factor 1 gene, complete cds, Human Fas antigen (fas) mRNA, complete cds, NEUTROPHIL OXIDASE FACTOR (p67 PHOX) (HUMAN), Human 11 kd protein mRNA, complete cds, Human semaphorin V mRNA, complete cds, MYELIN TRANSCRIPTION FACTOR 1 (HUMAN), 175991 NEURONAL CALCIUM SENSOR 1 (*Rattus norvegicus*), 81422 HUMAN SMOOTH MUSCLE ALPHA-ACTIN (AORTIC TYPE), Human mRNA for irp protein (int-l related protein), Human Fas antigen (fas) mRNA, complete cds, Human beta-migrating plasminogen activator inhibitor 1 mRNA 3' end, 26063 COMPLEMENT C4 PRECURSOR (*Homo sapiens*), 142450 VASCULAR ENDOTHELIAL GROWTH FACTOR PRECURSOR (*Rattus norvegicus*), Human visinin-like peptide 1 homolog mRNA, complete cds, *H. sapiens* mRNA for red cell anion exchanger (EPB3, Ael, Band 3) 3' non-coding region, Human laminin S B3 chain (LAMB3) mRNA, complete cds, Human cytochrome P450 IID6 (CYP2D6) gene, complete cds, Human hexokinase 1 (HK1) mRNA, complete cds, Human mRNA for the MDM2 gene, Human mRNA for cytochrome P-450LTBV, RYANODINE RECEPTOR, SKELETAL MUSCLE (HUMAN) 39052 POTASSIUM CHANNEL PROTEIN EAG (*Drosophila melanogaster*), and 124416 SERINE THREONINE-PROTEIN KINASE COT-1 (*Neurospora crassa*), and the second group consists of 196105 PLACENTAL CALCIUM-BINDING PROTEIN (HUMAN), 127228 HEAT SHOCK PROTEIN, CHAPERONIN 10, or GroES; MITOCHONDRIAL, *H. sapiens* Id1 mRNA, 51894 GTP-BINDING NUCLEAR PROTEIN RAN (*Homo sapiens*), 84680 ATP SYNTHASE ALPHA CHAIN, MITOCHONDRIAL PRECURSOR (HUMAN), Human non-histone chromosomal protein HMG-17 mRNA, complete cds, PHOSPHOGLYCERATE MUTASE, BRAIN FORM (HUMAN), Human mRNA (KIAAO108) for ORF (complete cds) and HepG2 mRNA identical sequence, 115413 HEAT SHOCK PROTEIN HSP 84 (*Mus musculus*), 78161 PROFILIN I (HUMAN), 124693 RAT mRNA for PROTEASOME SUBUNIT RC10–11, or HUMAN PROTEASOME SUBUNIT HSC10–11, 131036 TRANSFERRIN RECEPTOR PROTEIN (*Homo sapiens*), 214923 PSORIASIS-ASSOCIATED FATTY ACID BINDING PROTEIN HOMOLOG (HUMAN), Human mRNA (KIAA0098) for ORF (human counterpart of mouse chaperonin containing TCP-1 gene), partial cds, Human mRNA for ORF(KIAA0101), complete cds, 274422 ATPASE INHIBITOR, MITOCHONDRIAL (BOVIN), Human hnRNP A2 protein mRNA, 46019 MCM3 HOMOLOG (HUMAN), Human Ku autoimmune antigen gene, complete cds, Homo sapiens pstl mRNA for pancreatic secretory inhibitor (expressed in neoplastic tissue), Human esterase D mRNA 3'end, 49970 LUPUS LA PROTEIN (HUMAN), H. sapiens mRNA for TRAP beta subunit, 125446 TRANSCRIPTION INITIATION FACTOR TFIID (Homo sapiens), Human mRNA for human homologue of rat phosphatidylethanolamine binding protein, complete cds, 120041 HLA-DR ASSOC. PROTEIN I, P31 (also called Ii, In, M1, Dr gamma, XM 1) (Homo sapiens), Human protein-tyrosine phosphatase (HU-PP-1) mRNA, partial sequence, Homo sapiens integral nuclear envelope inner membrane protein (LBR) gene, complete cds, 52626 HYPOTHETICAL GTP-BINDING PROTEIN IN PMI40-PAC2 INTERGENIC REGION (Saccharomyces cerevisiae), H. sapiens mRNA for ATP-citrate lyase, Human mRNA for ORF (KIAA0102), complete cds, 238612 Human bumetanide-sensitive NA—K—Cl cotransporter (NKCC1 or BSC2) mRNA, complete cds, 26573 STATHMIN (Homo sapiens), H. sapiens mRNA for DNA primase (subunit p48), Human c-myb mRNA, 3'end, Human superoxide dismutase (SOD3 or EC-SOD) gene, complete cds, Human mRNA encoding IMP:pyrophosphate phosphoribosyltransferase E.C. 2.4.2.8, Human synexin mRNA, complete cds, Human p62 mRNA, complete cds, Human mRNA for mitochondrial 3-oxoacyl-CoA thiolase, complete cds, human mRNA (KIAA0094) for ORF (yeast methionine aminopeptidase-related), partial cds, 204299 REPLICATION PROTEIN A 14 KD SUBUNIT (HUMAN), H. sapiens mRNA for translin, 117708 MYOSIN HEAVY CHAIN, CLONE 203 (Hydra attenuata), Human mRNA (KIAA0088) for ORF (alpha-glucosidase-related), partial cds, Human mRNA (KIAA0035) for ORF (rat 140 kd nucleolar phosphoprotein homologue), partial cds, Human effector cell protease receptor-1 (EPR-1) gene, partial cds, 112020 C-1-TETRAHYDROFOLATE SYNTHASE, CYTOPLASMIC (HUMAN), 40874 TUBULIN GAMMA CHAIN (HUMAN), 42829 EUKARYOTIC INITATION FACTOR 4B (Homo sapiens), PROFILIN II (HUMAN), 40753 RAN-SPECIFIC GTPASE-ACTIVATING PROTEIN, ranGAP (Homo sapiens), Human mRNA for ORF (KIAK0002), or HUMAN D-TYPE CYCLIN complete cds, 128385 HAMSTER RNA FOR CYCLIN B2 (Mesocricetus auratus), PYRROLINE-5-CARBOXYLATE REDUCTASE (HUMAN), 150169 EUKARYOTIC INITIATION FACTOR 4E (Homo sapiens), 72050 NUCLEOTIDE-SENSITIVE CHLORIDE CHANNEL (Canis familaris), or HUMAN CHLORIDE CHANNEL REGULATORY PROTEIN mRNA, Homo sapiens CD24 signal transducer mRNA, complete cds and 3' region, H. sapiens mRNA for cathepsin C (dipeptidyl peptidase 1), Homo sapiens monocarboxylate transporter 1 (SLC161A1) mRNA, complete cds, 68690 U1 SMALL NCULEAR RIBONUCLEOPROTEIN A (HUMAN), Human serine kinase (SRPK1) mRNA, complete cds, 209484 CD9 ANTIGEN (Bos taurus), or HUMAN T245 PROTEIN, Human glutamate dehydrogenase (GDH) mRNA, complete cds, 109334 NEGATIVE REGULATOR OF MITOSIS (Emericella nidulans), 77138 EUKARYOTIC INITIATION FACTOR 1A (Sac cerevisiae), or HUMAN PROTEIN SYNTHESIS FACTOR 4C(elF-4C), H. sapiens mRNA for neuromedin U, Human chonndroitin/dermatan sulfate proteoglycan (PG40) core protein mRNA, complete cds, H. sapiens mRNA for 2'–5' oligoadenylate binding protein, Human mRNA (KIAA0024) for ORF (putative human counterpart of chinese hamster phosphatidylserine synthase gene), complete cds, Human MAC30 mRNA, 3'end, 74167 APOLIPOPROTEIN A-11 PRECURSOR (HUMAN), 36504 GTPASE ACTIVATING PROTEIN ROTUND (Drosophila melanogaster), 166353 CLEAVAGE STIMULATION FACTOR, 50 KD SUBUNIT (Homo sapiens), 127707 LAMININ BETA-1 CHAIN PRECURSOR (HUMAN), Human mRNA (KIAA0097) for ORF (novel protein), complete cds, 149556 O-antigen polymerase (Shigella flexneri), Homo sapiens E2F-related transcription factor (DP-1) mRNA, complete cds, NADH-UBIQUINONE DEHYDROGENASE 24 KD SUBUNIT PRECURSOR (HUMAN), Human methylmalonyl CoA mutase (MUT) gene, exon 13, 37866 BASIGIN PRECURSOR (Gallus gallus), 84443 GA BINDING PROTEIN BETA-1 CHAIN (Homo sapiens), Human erythroblastosis virus oncogene homolog 2 (ets-2) mRNA, complete cds, 53193 26S PROTEASE REGULATORY SUBUNIT 6 (Homo sapiens), S-ADENOSYLMETHIONINE DECARBOXYLASE PROENZYME (HUMAN), 26573 STATHMIN (Homo sapiens), 46827 VAV ONCOGENE (Homo sapiens), Human mRNA (KIAA0074) for ORF (yeast C728 protein-related), partial cds, Human DNA topoisomerase II gene (top2), gene 1, Homo sapiens cDNA clone 2531863', 151010 EUKARYOTIC PEPTIDE CHAIN RELASE FACTOR SUBUNIT 1 (Homo sapiens), Human medium-chain acyl-CoA dehydrogenase (ACADM) mRNA, complete cds, and 121357 A49436 CDI1=CYCLIN-DEPENDENT KINASE INTERACTOR 1, wherein a test substance is identified if it increases expression of a transcript which specifically hybridizes to a gene in the first group or decreases expression of a transcript which specifically hybridizes to a gene in the second group.

2. A method of screening to identify test substances which induce or repress genes which are induced or repressed by P53, comprising:

contacting a tumor cell which overexpresses MDM2 with a test substance;

monitoring expression of a transcript or its translation product, wherein the transcript specifically hybridizes to a gene selected from a first and a second group, wherein the first group consists of IG GAMMA-1 CHAIN C REGION (HUMAN), Human 1 g gamma3 heavy chain disease OMM protein mRNA, 274912 MYELIN TRANSCRIPTION FACTOR 1 (Homo sapiens), 152524 CYCLIN-DEPENDENT KINASE INHIBITOR 1 (Homo sapiens), H. sapiens mRNA for 43 kDa inositol polyphosphate 5-phosphatase, Human N-acetylgalactosamine 6-sulphatase (GALNS) gene, exon 14, 155730 KERATIN, TYPE I CYTOSKELETAL 17 (HUMAN), H. sapiens mRNA (clone 9112), kinase related protein, Human placenta cDNA coding for 5'nucleotidase (EC 3.1.3.5), H. sapiens MLN62 mRNA, Human activated p21cdc42Hs kinase (ack) mRNA, complete cds., 81780 COMPLEMENT C4 PRECURSOR (*Homo sapiens*), 172486 clone, mRNA for tuberin, or TSC2 gene, *Homo sapiens* of cardiac alpha-myosin heavy chain gene, KERATIN, TYPE II CYTOSKELETAL 5 (HUMAN); contains MSR1 repetive element, 182000 FK506-BINDING PROTEIN PRECURSOR (*Mus musculus*), Human insulin-like growth factor-binding protein-3 gene, complete Cds, clone HL1006d, 72466 ALPHA CRYSTALLIN B CHAIN (HUMAN), *Homo sapiens* mRNA for serum response factor-related protein, RSRFR2, 198656 HEPATOCYTE GROWTH FACTOR-LIKE PROTEIN PRECURSOR (*Homo sapiens*), 62461 SMALL NUCLEAR RIBONUCLEORPORTEIN Particle N (SNRPN), contains MSR1 repetive element, 155335 INTEGRIN ALPHA-3 (*Homo sapiens*), 41792 TUBULIN BETA-2 CHAIN (HUMAN), Human estradiol 17 beta-dehydrogenase gene, complete cds, *H. sapiens* mRNA for cystathionine-betasynthase, *Homo sapiens* of cardiac alpha-myosin heavy chain gene, Human mRNA for thyroglobulin, Human guanine nucleotide regulatory protein (ABR) mRNA, complete cds, Human novel growth factor receptor mRNA 3' Cds, 142899 DNA-DIRECTED RNA POLYMERASE III LARGEST SUBUNIT (*Plasmodium falciparum*), Human mRNA for collages VI alpha-1 C-terminal globular domain, *Homo sapiens* sodium channel type I, beta subunit (SCN1B) mRNA, complete cds., 50887 GUANINE NUCLEOTIDE DISSOCIATION STIMULATOR RALGDSA (*Mus musculus*), Human cytochrome P450 4F2 (CYP4F2) mRNA, complete cds, Human MAGE-2 gene exons 1–4, complete cds, *H. sapiens* mRNA for transforming growth factor alpha, 38251 *H. sapiens* HSJ1 mRNA, p53, *H. sapiens* mRNA for intestine-specific annexin, KERATIN, TYPE I CYTOSKELETAL 15 (HUMAN); contains MER20 repetitive element, 5065 GROWTH ARREST AND DNA-DAMAGE-INDUCIBLE PROTEIN GADD45 (*Homo sapiens*), Human steroidogenic acute regulatory protein (StAR) mRNA, complete cds, LYSYL HYDROXYLASE (PLOD), (HUMAN), 151767 FASL RECEPTOR PRECURSOR (*Homo sapiens*), *Homo sapiens* creatine transporter mRNA, complete cds, KERATIN TYPE I CYTOSKELETAL 15 (HUMAN); contains MER20 repetitive element, Human mRNA for thyroperoxidase, 275040 HEPATOCYTE GROWTH FACTOR-LIKE PROTEIN PRECURSOR (HUMAN), 121731 CYTOCHROME P450 IVB1 (*Rattus norvegicus*), *Homo sapiens* dopamine transporter (SLC6A3) mRNA, complete cds, 139080 COMPLEMENT DECAY-ACCELERATING FACTOR 1 PRECURSOR (*Homo sapiens*), *H. sapiens* mRNA for caveolin, Human endogenoous retrovirus type C onccovimus sequence, 31481 TYROSINE-PROTEIN KINASE HCK (*Homo sapiens*), *Homo sapiens* ribosomal protein S6 kinase 2 (RPS6KA2) mRNA, complete cds, Human Fas antigen (fas) mRNA, complete cds, Human mRNA encoding pregastrin (a regulatory hormone of gastric acid secretin and growth of the gastrointestinal mucosa), *H. sapiens* mRNA for placenta growth factor (PIGF), *H. sapiens* mRNA for placenta growth factor (PIGF), Human PML-2 mRNA, complete Cds, Human mRNA (KIAA0027) for ORF, partial cds, Human placenta-specific growth hormone mRNA, complete cds, Human high conductance inward rectifier potassium channel alpha subunit mRNA, complete cds, Human cytochrome P450 IID6 (CYP2D6) gene, complete cds, 180447 FIBROBLAST GROWTH FACTOR RECEPTOR 3 PRECURSOR (*Homo sapiens*), 153585 EBNA-2 NUCLEAR PROTEIN (Epstein-barr virus), 36678 TROPONIN C, ISOFORM 2 (*Balanus nubilis*), 182125 HDL-BINDING PROTEIN, HUMMLC2At; *Homo sapiens*: 593 base pairs, 80486 LIVER CARBOXYLESTERASE PRECURSOR (HUMAN), 121916 NEUTRAL CALPONIN, SMOOTH MUSCLE (*Sus scrofa*), Human 11 beta-hydroxysteroid dehydrogenase type II mRNA, complete cds, *Homo sapiens* interferon regulatory factor 1 gene, complete cds, Human Fas antigen (fas) mRNA, complete cds, NEUTROPHIL OXIDASE FACTOR (p67 PHOX) (HUMAN), Human 11 kd protein mRNA, complete cds, Human semaphorin V mRNA, complete cds, MYELIN TRANSCRIPTION FACTOR 1 (HUMAN), 175991 NEURONAL CALCUIM SENSOR 1 (*Rattus norvegicus*), 81422 HUMAN SMOOTH MUSCLE ALPHA-ACTIN (AORTIC TYPE), Human mRNA for irp protein (int-1 related protein), Human Fas antigen (fas) mRNA, complete cds, Human beta-migrating plasminogen activator inhibitor 1 mRNA 3' end, 26063 COMPLEMENT C4 PRECURSOR (*Homo sapiens*), 142450 VASCULAR ENDOTHELIAL GROWTH FACTOR PRECURSOR (*Rattus norvegicus*), Human visinin-like peptide 1 homologue mRNA, complete cds, *H. sapiens* mRNA for red cell anion exchanger (EPB3, Ael, Band 3) 3' non-coding region, Human laminin S B3 chain (LAMB3) mRNA, complete cds, Human cytochrome P450 IID6 (CYP2D6) gene, complete cds, Human hexokinase 1 (HK1) mRNA, complete cds, Human mRNA for the MDM2 gene, Human mRNA for cytochrome P-450LTBV, RYANODINE RECEPTOR, SKELETAL MUSCLE (HUMAN), 39052 POTASSIUM CHANNEL PROTEIN EAG (*Drosophila melanogaster*), and 124416 SERINE THREONINE-PROTEIN KINASE COT-1 (*Neurospora crassa*), and the second group consists of 196105 PLACENTAL CALCIUM-BINDING PROTEIN (HUMAN), 127228 HEAT SHOCK PROTEIN, CHAPERONIN 10, or GroES; MITOCHONDRIAL, *H. sapiens* Id1 mRNA, 51894 GTP-BINDING NUCLEAR PROTEIN RAN (*Homo sapiens*), 84680 ATP SYNTHASE ALPHA CHAIN, MITOCHONDRIAL PRECURSOR (HUMAN), Human non-histone chromosomal protein HMG-17 mRNA, complete cds, PHOSPHOGLYCERATE MUTASE, BRAIN FORM (HUMAN), Human mRNA (KIAAO108) for ORF (complete cds) and HepG2 mRNA identical sequence, 115413 HEAT SHOCK PROTEIN HSP 84 (*Mus musculus*), 78161 PROFILIN I (HUMAN), 124693 RAT mRNA for PROTEASOME SUBUNIT RC10–11, or HUMAN PROTEASOME SUBUNIT HSC10–11, 131036 TRANSFERRIN RECEPTOR PROTEIN (*Homo sapiens*), 214923 PSORIASIS-ASSOCIATED FATTY ACID BINDING PROTEIN HOMOLOG (HUMAN), Human mRNA (KIAA0098) for ORF (human counterpart of mouse chaperonin containing TCP-1 gene), partial cds, Human mRNA for ORF (KIAA0101), complete cds, 274422 ATPASE INHIBITOR, MITOCHONDRIAL (BOVIN), Human hnRNP A2 protein mRNA, 46019 MCM3 HOMOLOG (HUMAN), Human Ku autoimmune antigen gene, complete cds, *Homo sapiens* pstl mRNA for pancreatic secretory inhibitor (expressed in neoplastic tissue), Human esterase D mRNA 3'end, 49970 LUPUS LA PROTEIN (HUMAN), *H. sapiens* mRNA for TRAP beta subunit, 125446 TRANSCRIPTION INITIATION FACTOR TFIID (*Homo sapiens*), Human mRNA for human homologue of rat phosphatidylethanolamine binding protein, complete cds, 120041 HLA-DR ASSOC. PROTEIN I, P31 (also called Ii, In, M1, Dr gamma, XM 1) (*Homo sapiens*), Human protein-tyrosine phosphatase (HU-PP-1) mRNA, partial sequence, *Homo sapiens* integral nuclear envelope inner membrane protein (LBR) gene, complete cds, 52626 HYPOTHETICAL GTP-BINDING PROTEIN IN PMI40-PAC2 INTERGENIC REGION (*Saccharomyces cerevisiae*), *H. sapiens* mRNA for ATP-citrate lyase, Human mRNA for ORF (KIAA0102), complete cds, 238612 Human bumetanide-sensitive NA—K—Cl contransporter (NKCC1 or BSC2) mRNA, complete cds, 26573 STATHMIN (*Homo sapiens*), *H. sapiens* mRNA for DNA primase (subunit p48), Human c-myb mRNA, 3'end, Human superoxide dismutase (SOD3 or EC-SOD) gene, complete cds, Human mRNA encoding IMP:pyrophosphate phosphoribosyltransferase E.C. 2.4.2.8, Human synexin mRNA, complete cds, Human p62 mRNA, complete cds, Human mRNA for mitochondrial 3-oxoacyl-CoA thiolase, complete cds, Human mRNA (KIAA0094) for ORF (yeast methionine aminopeptidase-related), partial cds, 204299 REPLICATION PROTEIN A 14 KD SUBUNIT (HUMAN), *H. sapiens* mRNA for translin, 117708 MYOSIN HEAVY CHAIN, CLONE 203 (*Hydra attenuata*), Human mRNA (KIAA0088) for ORF (alpha-glucosidase-related), partial cds, Human mRNA (KIAA0035) for ORF (rat 140 kd nucleolar phosphoprotein homologue), partial cds, Human effector cell protease receptor-1 (EPR-1) gene, partial cds, 112020 C-1-TETRAHYDROFOLATE SYNTHASE, CYTOPLASMIC (HUMAN), 40874 TUBULIN GAMMA CHAIN (HUMAN), 42829 EUKARYOTIC INITATION FACTOR 4B (*Homo sapiens*), PROFILIN II (HUMAN), 40753 RAN-SPECIFIC GTPASE-ACTIVATING PROTEIN, ranGAP (*Homo sapiens*), Human mRNA for ORF (KIAK0002), or HUMAN D-TYPE CYCLIN complete cds, 128385 HAMSTER RNA FOR CYCLIN B2 (*Mesocricetus auratus*), PYRROLINE-5-CARBOXYLATE REDUCTASE (HUMAN), 150169 EUKARYOTIC INITIATION FACTOR 4E (*Homo sapiens*), 72050 NUCLEOTIDE-SENSITIVE CHLORIDE CHANNEL (*Canis familaris*), or HUMAN CHLORIDE CHANNEL REGULATORY PROTEIN mRNA, *Homo sapiens* CD24 signal transducer mRNA, complete cds and 3' region, *H. sapiens* mRNA for cathepsin C (dipeptidyl peptidase 1), *Homo sapiens* monocarboxylate transporter 1 (SLC161A1) mRNA, complete cds, 68690 U1 SMALL NUCLEAR RIBONUCLEOPROTEIN A (HUMAN), Human serine kinase (SRPK1) mRNA, complete cds, 209484 CD9 ANTIGEN (*Bos taurus*) or HUMAN T245 PROTEIN, Human glutamate dehydrogenase (GDH) mRNA, complete cds, 109334 NEGATIVE REGULATOR OF MITOSIS (*Emericella nidulans*), 77138 EUKARYOTIC INITIATION FACTOR 1A (*Sac cerevisiae*), or HUMAN PROTEIN SYNTHESIS FACTOR 4C (elF-4C), *H. sapiens* mRNA for neuromedin U, Human chonndroitin/dermatan sulfate proteoglycan (PG40) core protein mRNA, complete cds, *H. sapiens* mRNA for 2'–5' oligoadenylate binding protein, Human mRNA (KIAA0024) for ORF (putative human counterpart of chinese hamster phosphatidylserine synthase gene), complete cds, Human MAC30 mRNA, 3'end, 74167 APOLIPOPROTEIN A-11 PRECURSOR (HUMAN), 36504 GTPASE ACTIVATING PROTEIN ROTUND (*Drosophila melanogaster*), 166353 CLEAVAGE STIMULATION FACTOR, 50 KD SUBUNIT (*Homo sapiens*), 127707 LAMININ BETA-1 CHAIN PRECURSOR (HUMAN), Human mRNA (KIAA0097) for ORF (novel protein), complete cds, 149556 O-antigen polymerase (*Shigella flexneri*), *Homo sapiens* E2F-related transcription factor (DP-1) mRNA, complete cds, NADH-UBIQUINONE DEHYDROGENASE 24 KD SUBUNIT PRECURSOR (HUMAN), Human methylmalonyl CoA mutase (MUT) gene, exon 13, 37866 BASIGIN PRECURSOR (*Gallus gallus*), 84443 GA BINDING PROTEIN BETA-1 CHAIN (*Homo sapiens*), Human erythroblastosis virus oncogene homolog 2 (ets-2) mRNA, complete cds, 53193 26S PROTEASE REGULATORY SUBUNIT 6 (*Homo sapiens*), S-ADENOSYLMETHIONINE DECARBOXYLASE PROENZYME (HUMAN), 26573 STATHMIN (*Homo sapiens*), 46827 VAV ONCOGENE (*Homo sapiens*), Human mRNA (KIAA0074) for ORF (yeast C728 protein-related), partial cds, Human DNA topoisomerase II gene (top2), gene 1, *Homo sapiens* cDNA clone 253186 3', 151010 EUKARYOTIC PEPTIDE CHAIN RELASE FACTOR SUBUNIT 1 (*Homo sapiens*), Human medium-chain acyl-CoA dehydrogenase (ACADM) mRNA, complete cds, and 121357 A49436 CDI1=CYCLIN-DEPENDENT KINASE INTERACTOR 1, wherein a test substance is identified if it increases expression of a transcript which specifically hybridizes to a gene in the first group or decreases expression of a transcript which specifically hybridizes to a gene in the second group.

3. The method of claim 1 wherein the transcript specifically hybridizes to a gene selected from the first group.

4. The method of claim 1 wherein the transcript specifically hybridizes to a gene selected from the second group.

5. The method of claim 2 wherein the transcript specifically hybridizes to a gene selected from the first group.

6. The method of claim 2 wherein the transcript specifically hybridizes to a gene selected from the second group.

7. The method of claim 1 wherein the transcript specifically hybridizes to a gene selected from the group consisting of IG GAMMA-1 CHAIN C REGION (HUMAN), Human 1 g gamma3 heavy chain disease OMM protein mRNA, 274912 MYELIN TRANSCRIPTION FACTOR 1 (*Homo sapiens*), 152524 CYCLIN-DEPENDENT KINASE INHIBITOR 1 (*Homo sapiens*), *H. sapiens* mRNA for 43 kDa inositol polyphosphate 5-phosphatase, Human N-acetylgalactosamine 6-sulphatase (GALNS) gene, exon 14, 155730 KERATIN, TYPE I CYTOSKELETAL 17 (HUMAN), *H. sapiens* mRNA (clone 9112), kinase related protein, Human placental cDNA coding for 5'nucleotidase (EC 3.1.3.5), *H. sapiens* MLN62 mRNA, Human activated p21cdc42Hs kinase (ack) mRNA, complete cds., 81780 COMPLEMENT C4 PRECURSOR (*Homo sapiens*), 172486 clone, mRNA for tuberin, or TSC2 gene, *Homo sapiens* of cardiac alpha-myosin heavy chain gene, KERATIN, TYPE II CYTOSKELETAL 5 (HUMAN); contains MSR1 repetive element, and 182000 FK506-BINDING PROTEIN PRECURSOR (*Mus musculus*).

8. The method of claim 1 wherein the transcript specifically hybridizes to a gene selected from the group consisting of Human insulin-like growth factor-binding protein-3 gene, complete Cds, clone HL1006d, 72466 ALPHA CRYSTALLIN B CHAIN (HUMAN), *Homo sapiens* mRNA for serum response factor-related protein, RSRFR2, 198656 HEPATOCYTE GROWTH FACTOR-LIKE PROTEIN PRECURSOR (*Homo sapiens*), 62461 SMALL NUCLEAR RIBONUCLEORPORTEIN Particle N (SNRPN), contains MSR1 repetive element, 155335 INTEGRIN ALPHA-3 (*Homo sapiens*), 41792 TUBULIN BETA-2 CHAIN (HUMAN), Human estradiol 17 beta-dehydrogenase gene, complete cds, *H. sapiens* mRNA for cystathionine-betasynthase, *Homo sapiens* of cardiac alpha-myosin heavy chain gene, Human mRNA for thyroglobulin, Human guanine nucleotide regulatory protein (ABR) mRNA, complete cds, Human novel growth factor receptor mRNA 3' Cds, and 142899 DNA-DIRECTED RNA POLYMERASE III LARGEST SUBUNIT (*Plasmodium falciparum*).

9. The method of claim 1 wherein the transcript specifically hybridizes to a gene selected from the group consisting of Human mRNA for collagen VI alpha-1 C-terminal globular domain, *Homo sapiens* sodium channel type I, beta subunit (SCN1B) mRNA, complete cds., 50887 GUANINE NUCLEOTIDE DISSOCIATION STIMULATOR RALGDSA (*Mus musculus*), Human cytochrome P450 4F2 (CYP4F2) mRNA, complete cds, Human MAGE-2 gene exons 1–4, complete cds, *H. sapiens* mRNA for transforming growth factor alpha, 38251 *H sapiens* HSJ1 mRNA, p53, *H. sapiens* mRNA for intestine-specific annexin, KERATIN, TYPE I CYTOSKELETAL 15 (HUMAN); contains MER20 repetitive element, 5065 GROWTH ARREST AND DNA-DAMAGE-INDUCIBLE PROTEIN GADD45 (*Homo sapiens*), Human steroidogenic acute regulatory protein (StAR) mRNA, complete cds, LYSYL HYDROXYLASE (PLOD), (HUMAN), 151767 FASL RECEPTOR PRECURSOR (*Homo sapiens*), and *Homo sapiens* creatine transporter mRNA, complete cds.

10. The method of claim 1 wherein the transcript specifically hybridizes to a gene selected from the group consisting of KERATIN TYPE I CYTOSKELETAL 15 (HUMAN); contains MER20 repetitive element, Human mRNA for thyroperoxidase, 275040 HEPATOCYTE GROWTH FACTOR-LIKE PROTEIN PRECURSOR (HUMAN), 121731 CYTOCHROME P450 IVB1 (*Rattus norvegicus*), *Homo sapiens* dopamine transporter (SLC6A3) mRNA, complete cds, 139080 COMPLEMENT DECAY-ACCELERATING FACTOR 1 PRECURSOR (*Homo sapiens*), *H. sapiens* mRNA for caveolin, Human endogenoous retrovirus type C onccovirus sequence, 31481 TYROSINE-PROTEIN KINASE HCK (*Homo sapiens*), *Homo sapiens* ribosomal protein S6 kinase 2 (RPS6KA2) mRNA, complete cds, Human Fas antigen (fas) mRNA, complete cds, Human mRNA encoding pregastrin (a regulatory hormone of gastric acid secretin and growth of the gastrointestinal mucosa), *H. sapiens* mRNA for placenta growth factor (PIGF), *H. sapiens* mRNA for placenta growth factor (PIGF), Human PML-2 mRNA, complete Cds, Human mRNA (KIAA0027) for ORF, partial cds, Human placenta-specific growth hormone mRNA, complete cds, Human high conductance inward rectifier potassium channel alpha subunit mRNA, complete cds, Human cytochrome P450 IID6 (CYP2D6) gene, complete cds, 180447 FIBROBLAST GROWTH FACTOR RECEPTOR 3 PRECURSOR (*Homo sapiens*), 153585 EBNA-2 NUCLEAR PROTEIN (Epstein-barr virus), 36678 TROPONIN C, ISOFORM 2 (*Balanus nubilis*), 182125 HDL-BINDING PROTEIN, HUMMLC2At; *Homo sapiens*: 593 base pairs, 80486 LIVER CARBOXYLESTERASE PRECURSOR (HUMAN), and 121916 NEUTRAL CALPONIN, SMOOTH MUSCLE (*Sus scrofa*).

11. The method of claim 1 wherein the transcript specifically hybridizes to a gene selected from the group consisting of Human 11 beta-hydroxysteroid dehydrogenase type II mRNA, complete cds, *Homo sapiens* interferon regulatory factor 1 gene, complete cds, Human Fas antigen (fas) mRNA, complete cds, NEUTROPHIL OXIDASE FACTOR (p67 PHOX) (HUMAN), Human 11 kd protein mRNA, complete cds, Human semaphorin V mRNA, complete cds, MYELIN TRANSCRIPTION FACTOR 1 (HUMAN), 175991 NEURONAL CALCIUM SENSOR 1 (*Rattus norvegicus*), 81422 HUMAN SMOOTH MUSCLE ALPHA-ACTIN (AORTIC TYPE), Human mRNA for irp protein (int-1 related protein), Human Fas antigen (fas) mRNA, complete cds, Human beta-migrating plasminogen activator inhibitor 1 mRNA 3' end, 26063 COMPLEMENT C4 PRECURSOR (*Homo sapiens*), 142450 VASCULAR ENDOTHELIAL GROWTH FACTOR PRECURSOR (*Rattus norvegicus*), Human visinin-like peptide 1 homolog mRNA, complete cds, *H. sapiens* mRNA for red cell anion exchanger (EPB3, Ael, Band 3) 3' non-coding region, Human laminin S B3 chain (LAMB3) mRNA, complete cds, Human cytochrome P450 IID6 (CYP2D6) gene, complete cds, Human hexokinase 1 (HK 1) mRNA, complete cds, Human mRNA for the MDM2 gene, Human mRNA for cytochrome P-450LTBV, RYANODINE RECEPTOR, SKELETAL MUSCLE (HUMAN), 39052 POTASSIUM CHANNEL PROTEIN EAG (*Drosophila melanogaster*), and 124416 SERINE THREONINE-PROTEIN KINASE COT-1 (*Neurospora crassa*).

12. The method of claim 1 wherein the transcript specifically hybridizes to a gene selected from the group consisting of 196105 PLACENTAL CALCIUM-BINDING PROTEIN (HUMAN), 127228 HEAT SHOCK PROTEIN, CHAPERONIN 10, or GroES; MITOCHONDRIAL, *H. sapiens* Id1 mRNA, 51894 GTP-BINDING NUCLEAR PROTEIN RAN (*Homo sapiens*), 84680 ATP SYNTHASE ALPHA CHAIN, MITOCHONDRIAL PRECURSOR (HUMAN), Human non-histone chromosomal protein HMG-17 mRNA, complete cds, PHOSPHOGLYCERATE MUTASE, BRAIN FORM (HUMAN), Human mRNA (KIAAO108) for ORF (complete cds) and HepG2 mRNA identical sequence, 115413 HEAT SHOCK PROTEIN HSP 84 (*Mus musculus*), 78161 PROFILIN I (HUMAN), 124693 RAT mRNA for PROTEASOME SUBUNIT RC10–11, or HUMAN PROTEASOME SUBUNIT HSC10–11, 131036 TRANSFERRIN RECEPTOR PROTEIN (*Homo sapiens*), 214923 PSORIASIS-ASSOCIATED FATTY ACID BINDING PROTEIN HOMOLOG (HUMAN), Human mRNA (KIAA0098) for ORF (human counterpart of mouse chaperonin containing TCP-1 gene), partial cds, Human mRNA for ORF(KIAA0101), complete cds, 274422 ATPASE INHIBITOR, MITOCHONDRIAL (BOVIN), Human hnRNP A2 protein mRNA, 46019 MCM3 HOMOLOG (HUMAN), Human Ku autoimmune antigen gene, complete cds, *Homo sapiens* pstl mRNA for pancreatic secretory inhibitor (expressed in neoplastic tissue), Human esterase D mRNA 3'end, 49970 LUPUS LA PROTEIN (HUMAN), *H. sapiens* mRNA for TRAP beta subunit, and 125446 TRANSCRIPTION INITIATION FACTOR TFIID (*Homo sapiens*).

13. The method of claim 1 wherein the transcript specifically hybridizes to a gene selected from the group consisting of Human mRNA for human homologue of rat phosphatidylethanolamine binding protein, complete cds, 120041 HLA-DR ASSOC. PROTEIN I, P31 (also called Ii, In, M1, Dr gamma, XM 1) (*Homo sapiens*), Human protein-tyrosine phosphatase (HU-PP-1) mRNA, partial sequence, *Homo sapiens* integral nuclear envelope inner membrane protein (LBR) gene, complete cds, 52626 HYPOTHETICAL GTP-BINDING PROTEIN IN PMI40-PAC2 INTERGENIC REGION (*Saccharomyces cerevisiae*), *H. sapiens* mRNA for ATP-citrate lyase, Human mRNA for ORF (KIAA0102), complete cds, 238612 Human bumetanide-sensitive NA—K—Cl cotransporter (NKCC1 or BSC2) mRNA, complete cds, 26573 STATHMIN (*Homo sapiens*), *H. sapiens* mRNA for DNA primase (subunit p48), Human c-myb mRNA, 3'end, Human superoxide dismutase (SOD3 or EC-SOD) gene, complete cds, Human mRNA encoding IMP:pyrophosphate phosphoribosyltransferase E.C. 2.4.2.8, Human synexin mRNA, complete cds, Human p62 mRNA, complete cds, Human mRNA for mitochondrial 3-oxoacyl-CoA thiolase, complete cds, Human mRNA (KIAA0094) for ORF (yeast methionine aminopeptidase-related), partial cds, 204299 REPLICATION PROTEIN A 14 KD SUBUNIT (HUMAN), *H. sapiens* mRNA for translin, 117708 MYOSIN HEAVY CHAIN, CLONE 203 (Hydra attenuata), Human mRNA (KIAA0088) for ORF (alpha-glucosidase-related), partial cds, Human mRNA (KIAA0035) for ORF (rat 140 kd nucleolar phosphoprotein homologue), partial cds, Human effector cell protease receptor-1 (EPR-1) gene, partial cds, 112020 C-1-TETRAHYDROFOLATE SYNTHASE, CYTOPLASMIC (HUMAN), and 40874 TUBULIN GAMMA CHAIN (HUMAN).

14. The method of claim 1 wherein the transcript specifically hybridizes to a gene selected from the group consisting of 42829 EUKARYOTIC INITIATION FACTOR 4B (*Homo sapiens*), PROFILIN II (HUMAN), 40753 RAN-SPECIFIC GTPASE-ACTIVATING PROTEIN, ranGAP (*Homo sapiens*), Human mRNA for ORF (KIAK0002), or HUMAN D-TYPE CYCLIN complete cds, 128385 HAMSTER RNA FOR CYCLIN B2 (*Mesocricetus auratus*), PYRROLINE-5-CARBOXYLATE REDUCTASE (HUMAN), 150169 EUKARYOTIC INITIATION FACTOR 4E (*Homo sapiens*), 72050 NUCLEOTIDE-SENSITIVE CHLORIDE CHANNEL (*Canis familaris*), or HUMAN CHLORIDE CHANNEL REGULATORY PROTEIN mRNA, *Homo sapiens* CD24 signal transducer mRNA, complete cds and 3' region, *H. sapiens* mRNA for cathepsin C (dipeptidyl peptidase 1), *Homo sapiens* monocarboxylate transporter 1 (SLC161A1) mRNA, complete cds, 68690 U1 SMALL NUCLEAR RIBONUCLEOPROTEIN A (HUMAN), Human serine kinase (SRPK1) mRNA, complete cds, 209484 CD9 ANTIGEN (*Bos taurus*), or HUMAN T245 PROTEIN, and Human glutamate dehydrogenase (GDH) mRNA, complete cds.

15. The method of claim 1 wherein the transcript specifically hybridizes to a gene selected from the group consisting of 109334 NEGATIVE REGULATOR OF MITOSIS (*Emericella nidulans*), 77138 EUKARYOTIC INITIATION FACTOR 1A (*Sac cerevisiae*), or HUMAN PROTEIN SYNTHESIS FACTOR 4C(eIF-4C), *H. sapiens* mRNA for neuromedin U, Human chonndroitin/dermatan sulfate proteoglycan (PG40) core protein mRNA, complete cds, *H. sapiens* mRNA for 2'–5' oligoadenylate binding protein, Human mRNA (KIAA0024) for ORF (putative human counterpart of chinese hamster phosphatidylserine synthase gene), complete cds, Human MAC30 mRNA, 3' end, 74167 APOLIPOPROTEIN A-11 PRECURS0R (HUMAN), 36504 GTPASE ACTIVATING PROTEIN ROTUND (*Drosophila melanogaster*), 166353 CLEAVAGE STIMULATION FACTOR, 50 KD SUBUNIT (*Homo sapiens*), 127707 LAMININ BETA-1 CHAIN PRECURSOR (HUMAN), Human mRNA (KIAA0097) for ORF (novel protein), complete cds, 149556 O-antigen polymerase (*Shigella flexneri*), *Homo sapiens* E2F-related transcription factor (DP-1) mRNA, complete cds, NADH-UBIQUINONE DEHYDROGENASE 24 KD SUBUNIT PRECURSOR (HUMAN), Human methylmalonyl CoA mutase (MUT) gene, exon 13, 37866 BASIGIN PRECURSOR (*Gallus gallus*), 84443 GA BINDING PROTEIN BETA-1 CHAIN (*Homo sapiens*), Human erythroblastosis virus oncogene homolog 2 (ets-2) mRNA, complete cds, 53193 26S PROTEASE REGULATORY SUBUNIT 6 (*Homo sapiens*), S-ADENOSYLMETHIONINE DECARBOXYLASE PROENZYME (HUMAN), 26573 STATHMIN (*Homo sapiens*), 46827 VAV ONCOGENE (*Homo sapiens*), Human mRNA (KIAA0074) for ORF (yeast C728 protein-related), partial cds, Human DNA topoisomerase II gene (top2), gene 1, *Homo sapiens* cDNA clone 253186 3', 151010 EUKARYOTIC PEPTIDE CHAIN RELEASE FACTOR SUBUNIT 1 (*Homo sapiens*), Human medium-chain acyl-CoA dehydrogenase (ACADM) mRNA, complete cds, and 121357 A49436 CDI1=CYCLIN-DEPENDENT KINASE INTERACTOR 1.

16. The method of claim 2 wherein the transcript specifically hybridizes to a gene selected from the group consisting of IG GAMMA-1 CHAIN C REGION (HUMAN), Human 1 g gamma3 heavy chain disease OMM protein mRNA, 274912 MYELIN TRANSCRIPTION FACTOR 1 (*Homo sapiens*), 152524 CYCLIN-DEPENDENT KINASE INHIBITOR 1 (*Homo sapiens*), *H. sapiens* mRNA for 43 kDa inositol polyphosphate 5-phosphatase, Human N-acetylgalactosamine 6-sulphatase (GALNS) gene, exon 14, 155730 KERATIN, TYPE I CYTOSKELETAL 17 (HUMAN), *H. sapiens* mRNA (clone 9112), kinase related protein, Human placental cDNA coding for 5'nucleotidase (EC 3.1.3.5), *H. sapiens* MLN62 mRNA, Human activated p21cdc42Hs kinase (ack) mRNA, complete cds., 81780 COMPLEMENT C4 PRECURSOR (*Homo sapiens*), 172486 clone, mRNA for tuberin, or TSC2 gene, *Homo sapiens* of cardiac alpha-myosin heavy chain gene, KERATIN, TYPE II CYTOSKELETAL 5 (HUMAN); contains MSR1 repetive element, and 182000 FK506-BINDING PROTEIN PRECURSOR (*Mus musculus*).

17. The method of claim 2 wherein the transcript specifically hybridizes to a gene selected from the group consisting of Human insulin-like growth factor-binding protein-3 gene, complete Cds, clone HL1006d, 72466 ALPHA CRYSTALLIN B CHAIN (HUMAN), *Homo sapiens* mRNA for serum response factor-related protein, RSRFR2, 198656 HEPATOCYTE GROWTH FACTOR-LIKE PROTEIN PRECURSOR (*Homo sapiens*), 62461 SMALL NUCLEAR RIBONUCLEOPROTEIN Particle N (SNRPN), contains MSR1 repetive element, 155335 INTEGRIN ALPHA-3 (*Homo sapiens*), 41792 TUBULIN BETA-2 CHAIN (HUMAN), Human estradiol 17 beta-dehydrogenase gene, complete cds, *H. sapiens* mRNA, for cystathionine-betasynthase, *Homo sapiens* of cardiac alpha-myosin heavy chain gene, Human mRNA for thyroglobulin, Human guanine nucleotide regulatory protein (ABR) mRNA, complete cds, Human novel growth factor receptor mRNA 3' Cds, and 142899 DNA-DIRECTED RNA POLYMERASE III LARGEST SUBUNIT (*Plasmodium falciparum*).

18. The method of claim 2 wherein the transcript specifically hybridizes to a gene selected from the group consisting of Human mRNA for collagen VI alpha-1 C-terminal globular domain, *Homo sapiens* sodium channel type I, beta subunit (SCN1B) mRNA, complete cds., 50887 GUANINE NUCLEOTIDE DISSOCIATION STIMULATOR RAL- GDSA (*Mus musculus*), Human cytochrome P450 4F2 (CYP4F2) mRNA, complete cds, Human MAGE-2 gene exoris 1–4, complete cds, *H. sapiens* mRNA for transforming growth factor alpha, 38251 *H sapiens* HSJ1 mRNA, p53, *H. sapiens* mRNA for intestine-specific annexin, KERATIN, TYPE I CYTOSKELETAL 15 (HUMAN); contains MER20 repetitive element, 5065 GROWTH ARREST AND DNA-DAMAGE-INDUCIBLE PROTEIN GADD45 (*Homo sapiens*), Human steroidogenic acute regulatory protein (StAR) mRNA, complete cds, LYSYL HYDROXYLASE (PLOD), (HUMAN), 151767 FASL RECEPTOR PRECURSOR (*Homo sapiens*), and *Homo sapiens* creatine transporter mRNA, complete cds.

19. The method of claim 2 wherein the transcript specifically hybridizes to a gene selected from the group consisting of KERATIN TYPE I CYTOSKELETAL 15 (HUMAN); contains MER20 repetitive element, Human mRNA for thyroperoxidase, 275040 HEPATOCYTE GROWTH FACTOR-LIKE PROTEIN PRECURSOR (HUMAN), 121731 CYTOCHROME P450 IVB1 (*Rattus norvegicus*), *Homo sapiens* dopamine transporter (SLC6A3) mRNA, complete cds, 139080 COMPLEMENT DECAY-ACCELERATING FACTOR 1 PRECURSOR (*Homo sapiens*), *H. sapiens* mRNA for caveolin, Human endogenoous retrovirus type C onccovirus sequence, 31481 TYROSINE-PROTEIN KINASE HCK (*Homo sapiens*), *Homo sapiens* ribosomal protein S6 kinase 2 (RPS6KA2) mRNA, complete cds, Human Fas antigen (fas) mRNA, complete cds, Human mRNA encoding pregastrin (a regulatory hormone of gastric acid secretin and growth of the gastrointestinal mucosa), *H. sapiens* mRNA for placenta growth factor (PIGF), *H. sapiens* mRNA for placenta growth factor (PIGF), Human PML-2 mRNA, complete Cds, Human mRNA (KIAA0027) for ORF, partial cds, Human placenta-specific growth hormone mRNA, complete cds, Human high conductance inward rectifier potassium channel alpha subunit mRNA, complete cds, Human cytochrome P450 IID6 (CYP2D6) gene, complete cds, 180447 FIBROBLAST GROWTH FACTOR RECEPTOR 3 PRECURSOR (*Homo sapiens*), 153585 EBNA-2 NUCLEAR PROTEIN (Epstein-barr virus), 36678 TROPONIN C, ISOFORM 2 (*Balanus nubilis*), 182125 HDL-BINDING PROTEIN, FUMMLC2At; *Homo sapiens*: 593 base pairs, 80486 LIVER CARBOXYLESTERASE PRECURSOR (HUMAN), and 121916 NEUTRAL CALPONIN, SMOOTH MUSCLE (*Sus scrofa*).

20. The method of claim 2 wherein the transcript specifically hybridizes to a gene selected from the group consisting of Human 11 beta-hydroxysteroid dehydrogenase type II mRNA, complete cds, *Homo sapiens* interferon regulatory factor 1 gene, complete cds, Human Fas antigen (fas) mRNA, complete cds, NEUTROPHIL OXIDASE FACTOR (p67 PHOX) (HUMAN), Human 11 kd protein mRNA, complete cds, Human semaphorin V mRNA, complete cds, MYELIN TRANSCRIPTION FACTOR 1 (HUMAN) 175991 NEURONAL CALCIUM SENSOR 1 (*Rattus norvegicus*), 81422 HUMAN SMOOTH MUSCLE ALPHA-ACTIN (AORTIC TYPE), Human mRNA for irp protein (int-1 related protein), Human Fas antigen (fas) mRNA, complete cds, Human beta-migrating plasminogen activator inhibitor 1 mRNA 3'end, 26063 COMPLEMENT C4 PRECURSOR (*Homo sapiens*), 142450 VASCULAR ENDOTHELIAL GROWTH FACTOR PRECURSOR (*Rattus norvegicus*), Human visinin-like peptide 1 homolog mRNA, complete cds, *H. sapiens* mRNA for red cell anion exchanger (EPB3, Ael, Band 3) 3' non-coding region, Human laminin S B3 chain (LAMB3) mRNA, complete cds, Human cytochrome P450 IID6 (CYP2D6) gene, complete cds, Human hexokinase 1 (HK1) mRNA, complete cds, Human mRNA for the MDM2 gene, Human mRNA for cytochrome P-450LTBV, RYANODINE RECEPTOR, SKELETAL MUSCLE (HUMAN), 39052 POTASSIUM CHANNEL PROTEIN EAG (*Drosophila melanogaster*), and 124416 SERINE THREONINE-PROTEIN KINASE COT-1 (*Neurospora crassa*).

21. The method of claim 2 wherein the transcript specifically hybridizes to a gene selected from the group consisting of 196105 PLACENTAL CALCIUM-BINDING PROTEIN (HUMAN), 127228 HEAT SHOCK PROTEIN, CHAPERONIN 10, or GroES; MITOCHONDRIAL, *H. sapiens* Id1 mRNA, 51894 GTP-BINDING NUCLEAR PROTEIN RAN (*Homo sapiens*), 84680 ATP SYNTHASE ALPHA CHAIN, MITOCHONDRIAL PRECURSOR (HUMAN), Human non-histone chromosomal protein HMG-17 mRNA, complete cds, PHOSPHOGLYCERATE MUTASE, BRAIN FORM (HUMAN), Human mRNA (KIAAO108) for ORF (complete cds) and HepG2 mRNA identical sequence, 115413 HEAT SHOCKPROTEIN HSP 84 (*Mus musculus*), 78161 PROFILIN I (HUMAN), 124693 RAT mRNA for PROTEASOME SUBUNIT RC10-11, or HUMAN PROTEASOME SUBUNIT HSC10-11, 131036 TRANSFERRIN RECEPTOR PROTEIN (*Homo sapiens*), 214923 PSORIASIS-ASSOCIATED FATTY ACID BINDING PROTEIN HOMOLOG (HUMAN), Human mRNA (KIAA0098) for ORF (human counterpart of mouse chaperonin containing TCP-1 gene), partial cds, Human mRNA for ORF(KIAA0101), complete cds, 274422 ATPASE INHIBITOR, MITOCHONDRIAL (BOVIN), Human hnRNP A2 protein mRNA, 46019 MCM3 HOMOLOG (HUMAN), Human Ku autoimmune antigen gene, complete cds, *Homo sapiens* pstl mRNA for pancreatic secretory inhibitor (expressed in neoplastic tissue), Human esterase D mRNA 3'end, 49970 LUPUS LA PROTEIN (HUMAN), *H. sapiens* mRNA for TRAP beta subunit, and 125446 TRANSCRIPTION INITIATION FACTOR TFIID (*Homo sapiens*).

22. The method of claim 2 wherein the transcript specifically hybridizes to a gene selected from the group consisting of Human mRNA for human homologue of rat phosphatidylethanolamine binding protein, complete cds, 120041 HLA-DR ASSOC. PROTEIN I, P31 (also called Ii, In, M1, Dr gamma, XM 1) (*Homo sapiens*), Human protein-tyrosine phosphatase (HU-PP-1) mRNA, partial sequence, *Homo sapiens* integral nuclear envelope inner membrane protein (LBR) gene, complete cds, 52626 HYPOTHETICAL GTP-BINDING PROTEIN IN PMI40-PAC2 INTERGENIC REGION (*Saccharomyces cerevisiae*), *H. sapiens* mRNA for ATP-citrate lyase, Human mRNA for ORF (KIAA0102), complete cds, 238612 Human bumetanide-sensitive NA—K—Cl cotransporter (NKCC1 or BSC2) mRNA, complete cds, 26573 STATHMIN (*Homo sapiens*), *H. sapiens* mRNA for DNA primase (subunit p48), Human c-myb mRNA, 3'end, Human superoxide dismutase (SOD3 or EC-SOD) gene, complete cds, Human mRNA encoding IMP:pyrophosphate phosphoribosyltransferase E.C. 2.4.2.8, Human synexin mRNA, complete cds, Human p62 mRNA, complete cds, Human mRNA for mitochondrial 3-oxoacyl-CoA thiolase, complete cds, Human mRNA (KIAA0094) for ORF (yeast methionine aminopeptidase-related), partial cds, 204299 REPLICATION PROTEIN A 14 KD SUBUNIT (HUMAN), *H. sapiens* mRNA for translin, 117708 MYOSIN HEAVY CHAIN, CLONE 203 (*Hydra attenuata*), Human mRNA (KIAA0088) for ORF (alpha-glucosidase-related), partial cds, Human mRNA (KIAA0035) for ORF (rat 140 kd nucleolar phosphoprotein homologue), partial cds, Human effector cell protease receptor-1 (EPR-1) gene, partial cds, 112020 C-1-TETRAHYDROFOLATE SYNTHASE, CYTOPLASMIC (HUMAN), and 40874 TUBULIN GAMMA CHAIN (HUMAN).

23. The method of claim 2 wherein the transcript specifically hybridizes to a gene selected from the group consisting of 42829 EUKARYOTIC INITATION FACTOR 4B (*Homo sapiens*), PROFILIN II (HUMAN), 40753 RAN-SPECIFIC GTPASE-ACTIVATING PROTEIN, ranGAP (*Homo sapiens*), Human mRNA for ORF (KIAK0002), or HUMAN D-TYPE CYCLIN complete cds, 128385 HAMSTER RNA FOR CYCLIN B2 (*Mesocricetus auratus*), PYRROLINE-5-CARBOXYLATE REDUCTASE (HUMAN), 150169 EUKARYOTIC INITIATION FACTOR 4E (*Homo sapiens*), 72050 NUCLEOTIDE-SENSITIVE CHLORIDE CHANNEL (*Canis familaris*), or HUMAN CHLORIDE CHANNEL REGULATORY PROTEIN mRNA, *Homo sapiens* CD24 signal transducer mRNA, complete cds and 3' region, *H. sapiens* mRNA for cathepsin C (dipeptidyl peptidase 1), *Homo sapiens* monocarboxylate transporter 1 (SLC161A1) mRNA, complete cds, 68690 U1 SMALL NUCLEAR RIBONUCLEOPROTEIN A (HUMAN), Human serine kinase (SRPK1) mRNA, complete cds, 209484 CD9 ANTIGEN (*Bos taurus*), or HUMAN T245 PROTEIN, and Human glutamate dehydrogenase (GDH) mRNA, complete cds.

24. The method of claim 2 wherein the transcript specifically hybridizes to a gene selected from the group consisting of 109334 NEGATIVE REGULATOR OF MITOSIS (*Emericella nidulans*), 77138 EUKARYOTIC INITIATION FACTOR 1A (*Sac cerevisiae*), or HUMAN PROTEIN SYNTHESIS FACTOR 4C(eIF-4C), *H. sapiens* mRNA for neuromedin U, Human chonndroitin/dermatan sulfate proteoglycan (PG40) core protein mRNA, complete cds, *H. sapiens* mRNA for 2'–5' oligoadenylate binding protein, Human mRNA (KIAA0024) for ORF (putative human counterpart of chinese hamster phosphatidylserine synthase gene), complete cds, Human MAC30 mRNA, 3' end, 74167 APOLIPOPROTEIN A-11 PRECURSOR (HUMAN), 36504 GTPASE ACTIVATING PROTEIN ROTUND (*Drosophila melanogaster*), 166353 CLEAVAGE STIMULATION FACTOR, 50 KD SUBUNIT (*Homo sapiens*), 127707 LAMININ BETA-1 CHAIN PRECURSOR (HUMAN), Human mRNA (KIAA0097) for ORF (novel protein), complete cds, 149556 O-antigen polymerase (*Shigella flexneri*), *Homo sapiens* E2F-related transcription factor (DP-1) mRNA, complete cds, NADH-UBIQUINONE DEHYDROGENASE 24 KD SUBUNIT PRECURSOR (HUMAN), Human methylmalonyl CoA mutase (MUT) gene, exon 13, 37866 BASIGIN PRECURSOR (*Gallus gallus*), 84443 GA BINDING PROTEIN BETA-1 CHAIN (*Homo sapiens*), Human erythroblastosis virus oncogene homolog 2 (ets-2) mRNA, complete cds, 53193 26S PROTEASE REGULATORY SUBUNIT 6 (*Homo sapiens*), S-ADENOSYLMETHIONINE DECARBOXYLASE PROENZYME (HUMAN), 26573 STATHMIN (*Homo sapiens*), 46827 VAV ONCOGENE (*Homo sapiens*), Human mRNA (KIAA0074) for ORF (yeast C728 protein-related), partial cds, Human DNA topoisomerase II gene (top2), gene 1, *Homo sapiens* cDNA clone 253186 3', 151010 EUKARYOTIC PEPTIDE CHAIN RELEASE FACTOR SUBUNIT 1 (*Homo sapiens*), Human medium-chain acyl-CoA dehydrogenase (ACADM) mRNA, complete cds, and 121357 A49436 CDI1=CYCLIN-DEPENDENT KINASE INTERACTOR 1.

* * * * *